(12) United States Patent
Mayer et al.

(10) Patent No.: US 6,939,886 B2
(45) Date of Patent: Sep. 6, 2005

(54) SUBSTITUTED NAPHTHYL INDOLE DERIVATIVES AS INHIBITORS OF PLASMINOGEN ACTIVATOR INHIBITOR TYPE-1 (PAI-1)

(75) Inventors: Scott Christian Mayer, Bridgewater, NJ (US); Eric Gould Gundersen, Royersford, PA (US); Hassan Mahmoud Elokdah, Yardley, PA (US); David LeRoy Crandall, Doylestown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/894,618

(22) Filed: Jul. 20, 2004

(65) Prior Publication Data

US 2004/0266733 A1 Dec. 30, 2004

Related U.S. Application Data

(63) Continuation of application No. 10/171,041, filed on Jun. 13, 2002, now Pat. No. 6,800,654.
(60) Provisional application No. 60/299,651, filed on Jun. 20, 2001.

(51) Int. Cl.[7] .................... A61K 31/404; C07D 209/04; C07D 403/02
(52) U.S. Cl. ................ 514/381; 548/243; 548/252; 548/413; 548/414; 548/491; 549/356; 549/414; 514/414; 514/415
(58) Field of Search ................ 548/252, 243, 548/413, 414, 491; 514/381, 414, 415; 549/414, 356

(56) References Cited

U.S. PATENT DOCUMENTS 5,151,435 A  9/1992 Bagley et al.

FOREIGN PATENT DOCUMENTS

| EP | 0 416 609 B1 | 3/1991 |
|---|---|---|
| EP | 0 508 723 A | 10/1992 |
| EP | 0 512 570 B1 | 11/1992 |
| EP | 0 655 439 A2 | 5/1995 |
| WO | WO 94/26738 A1 | 11/1994 |
| WO | WO 95/10513 A1 | 4/1995 |
| WO | WO 96/21656 A1 | 7/1996 |
| WO | WO 97/09308 A1 | 3/1997 |
| WO | WO 98/08818 A1 | 3/1998 |

OTHER PUBLICATIONS

Nordt et al., The Journal of Clinical Endocrinology & Metabolism, 85(4), 1563–1568 (2000).
Aznar et al., Haemostasis, 24 243–251 (1994).
Carmeliet et al., Journal of Clinical Invest., 92, 2756–2760 (1993).
Daci et al., Journal of Bone & Mineral Research, 15(8), 1510–1516 (2000).
Biemond et al., Circulation, 91(4), 1175–1181 (1995).
Levi et al., Circulation, 85(1), 305–312 (1992).
Rocha et al., Fibrinolysis, 8, 294–303 (1994).
Reilly et al., Arteriosclerosis & Thrombosis 11, 1276–1286 (1991).
Krishnamurti et al., Blood, 69(3), 798–803 (1987).
Guzzo, P.R. et al., Tetrahedron Letters, 43(1), 41–42 (2002).

*Primary Examiner*—Golam M M Shameem
(74) *Attorney, Agent, or Firm*—Woodcock Washburn LLP

(57) ABSTRACT

This invention provides PAI-1 inhibiting compounds of Formula I:

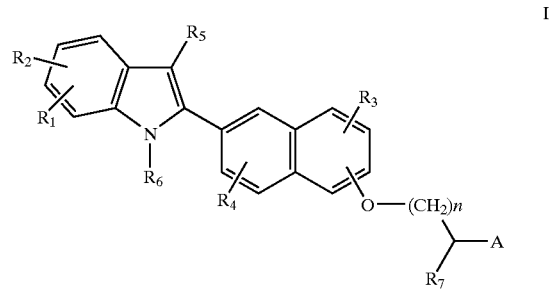

wherein: $R_1$, $R_2$, $R_3$, and $R_4$ are each H, alkyl, alkanoyl, halo, OH, aryl optionally substituted with $R_8$, perfluoroalkyl, alkoxy, amino, alkylamino, dialkylamino, perfluoroalkoxy; $R_5$ is H, alkyl, perfluoroalkyl, aryl optionally substituted with $R_8$, alkanoyl, aroyl optionally substituted with $R_8$; $R_6$ is H, alkyl, alkylaryl, benzyl optionally substituted with $R_8$, alkanoyl, aroyl optionally substituted with $R_8$; $R_7$ is H, alkyl, alkylaryl, aryl optionally substituted with $R_8$; n is 0–6; A is COOH, or an acid mimic such as tetraazole, $SO_3H$, $PO_3H_2$, tetronic acid, etc.; $R_8$ is H, alkyl, cycloalkyl, alkanoyl, halo, OH, perfluoroalkyl, alkoxy, amino, alkylamino, dialkylamino, perfluoroalkoxy; or a pharmaceutically acceptable salt thereof; as well as pharmaceutical compositions and methods of treatment using these compounds.

10 Claims, No Drawings

SUBSTITUTED NAPHTHYL INDOLE DERIVATIVES AS INHIBITORS OF PLASMINOGEN ACTIVATOR INHIBITOR TYPE-1 (PAI-1)

This application is a continuation of, and claims prionty under 35 U.S.C. §120, to U.S. patent application Ser. No. 10/171,041, filed Jun. 13, 2002, now U.S. Pat. No. 6,800,654, which, in turn, claims priority under 35 U.S.C. §119(e) to U.S. Provisional Application No. 60/299,651 filed Jun. 20, 2000.

This invention relates to the composition and utility of substituted naphthyl indole derivatives as inhibitors of plasminogen activator inhibitor-1 (PAI-1) and as therapeutic compositions for treating conditions resulting from fibrinolytic disorders such as deep vein thrombosis and coronary heart disease, and pulmonary fibrosis.

BACKGROUND OF THE INVENTION

Plasminogen activator inhibitor-1 (PAI-1) is a major regulatory component of the plasminogen-plasmin system. PAI-1 is the principal physiologic inhibitor of both tissue type plasminogen activator (tPA) and urokinase type plasminogen activator (uPA). Elevated plasma levels of PAI-1 have been associated with thrombotic events as indicated by animal experiments (Krishnamurti, *Blood*, 69, 798 (1987); Reilly, *Arteriosclerosis and Thrombosis*, 11, 1276 (1991); Carmeliet, *Journal of Clinical Investigation*, 92, 2756 (1993)) and clinical studies (Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases of women such as polycystic ovary syndrome (Nordt, *Journal of clinical Endocrinology and Metabolism*, 85, 4, 1563 (2000)) and bone loss induced by estrogen deficiency (Daci, *Journal of Bone and Mineral Research*, 15, 8, 1510 (2000)). Accordingly, agents that inhibit PAI-1 would be of utility in treating conditions originating from fibrinolytic disorder such as deep vein thrombosis, coronary heart disease, pulmonary embolism, polycystic ovary syndrome, etc.

WO 98/08818 discloses substituted indoles and benzimidazoles of Formulas I, II, & III which are chemical inhibitors of various phospholipase enzymes (such as PLA$_2$) useful in the treatment of inflammation.

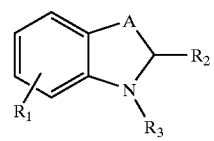

(I)

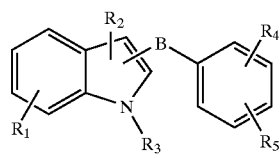

(II)

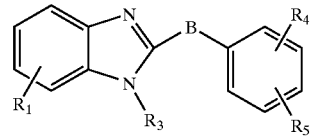

(III)

WO 96/21656 discloses compounds of Formula I which are useful for treating or preventing obesity, breast cancer, osteoporosis, endometriosis, cardiovascular disease and prostatic disease.

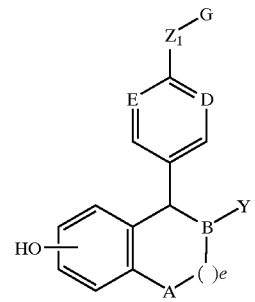

(I)

In addition, the utilities of the current invention are different.

EP 0 655 439 (Eli Lilly and Company) relates to 5,6 fused ring bicyclic compounds inclusive of indoles, benzofurans, and benzothiophenes corresponding to the general Formula I as platelet aggregation inhibitors.

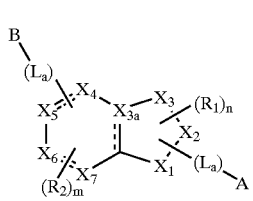

(I)

WO 95/10513 (Pfizer, Inc.) discloses substituted indoles, benzofurans, and benzthiophenes of Formula I as estrogen agonists which are useful for treating syndromes and diseases caused by estrogen deficiency.

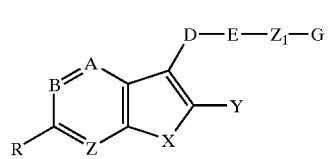

(I)

WO 94/26738 and EP 0 512 570 (Fujisawa Pharmaceutical Co., Ltd.) disclose the preparation of substituted indoles, benzofurans, and benzthiophenes (Formula I) which possess an inhibitory activity against ACAT (cholesterol acyltransferase enzyme) and are useful for the prevention and/or treatment of hypercholesterolemia, hyperlipidemia, atherosclerosis or diseases caused thereby.

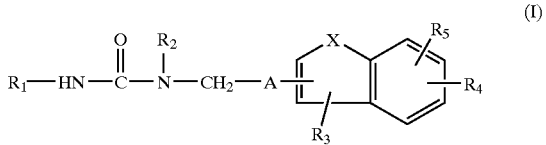

U.S. Pat. No. 5,151,435 discloses substituted imidazolo/benzimidazolo-indoles and dihydroindoles of Formula I which are useful as angiotensin II antagonists in the treatment of hypertension.

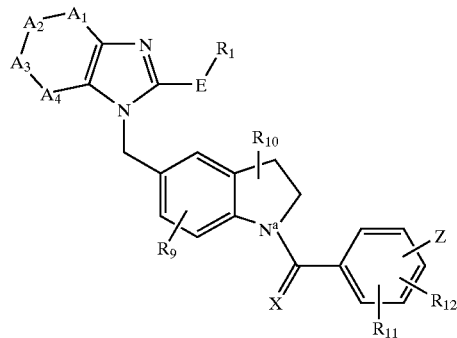

EP 0 416 609 discloses indole-, benzofuran-, and benzothiophene-containing lipoxygenase-inhibiting compounds (Formula I) as well as pro-drugs of these compounds having metabolically cleavable groups.

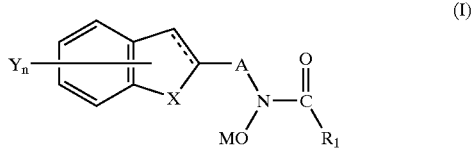

DESCRIPTION OF THE INVENTION

This invention comprises compounds of Formula I:

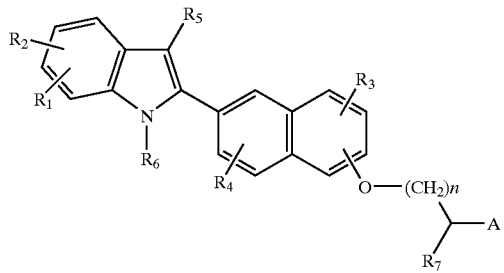

wherein:

$R_1$, $R_2$, $R_3$, and $R_4$ are each, independently, hydrogen, alkyl of 1–3 carbons, cycloalkyl of 3–5 carbon atoms, —$CH_2$-cycloalkyl of 3–5 carbon atoms, alkanoyl of 1–3 carbons, halogen, hydroxy, aryl optionally substituted with from 1 to 3 groups selected from $R_8$, perfluoroalkyl of 1–3 carbons, alkoxy of 1–3 carbons, amino, alkylamino of 1–3 carbons, dialkylamino of 1–3 carbons, perfluoroalkoxy of 1–3 carbons;

$R_5$ is hydrogen, alkyl of 1–6 carbons, perfluoroalkyl of 1–6 carbons, aryl substituted with $R_8$, alkanoyl of 1–6 carbons, aroyl optionally substituted with from 1 to 3 groups selected from $R_8$;

$R_6$ is hydrogen, alkyl of 1–6 carbons, alkylaryl, benzyl substituted with $R_8$, alkanoyl of 1–6 carbons, aroyl optionally substituted with from 1 to 3 groups selected from $R_8$;

$R_7$ is hydrogen, alkyl of 1–6 carbons, alkylaryl, aryl optionally substituted with from 1 to 3 groups selected from $R_8$;

n is an integer of 0–6;

A is COOH or an acid mimic such as tetraazole, $SO_3H$, $PO_3H_2$, tetronic acid, etc.;

$R_8$ is hydrogen, alkyl of 1–3 carbons, cycloalkyl of 3–5 carbons, —$CH_2$-cycloalkyl of 3–5 carbon atoms, alkanoyl of 1–3 carbons, halogen, hydroxy, perfluoroalkyl of 1–3 carbons, alkoxy of 1–3 carbons, amino, alkylamino of 1–3 carbons, dialkylamino of 1–3 carbons, perfluoroalkoxy of 1–3 carbons;

or a pharmaceutically acceptable salt or ester form thereof.

As used herein, alkyl includes both straight and branched alkyl moieties and halogen includes bromine, chlorine, fluorine, and iodine.

Ester forms of the compounds of this invention include the pharmaceutically acceptable ester forms known in the art for the acid groups of Formula I, above. These esters include straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters. Other non-limiting examples of esters useful with this invention include those wherein A is a carboxylic acid and the ester form has the formula —$COOR_9$ wherein $R_9$ is selected from the formulae:

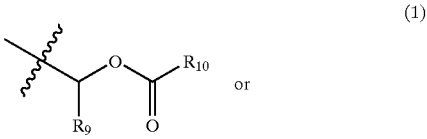

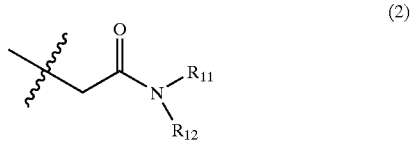

wherein $R_9$, $R_{10}$, $R_{11}$ and $R_{12}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Among the preferred ester forms of the compounds herein include but not limited to $C_1$–$C_6$ alkyl esters, $C_3$–$C_6$ branched alkyl esters, benzyl esters, etc.

Acid mimic or mimetics which are included in the acidic groups of this invention, as noted in the definition of A, above, particularly include the pharmaceutically useful carboxylic acid mimics or mimetics known in the art, such as those described in R. Silverman, The Organic Chemistry of Drug Design and Drug Action, Academic Press (1992), the contents of which are incorporated herein by reference. Non-limiting examples of these acid mimics include such as tetrazole, $SO_3H$, $PO_3H_2$, tetronic acid, etc., or groups having the formulae:

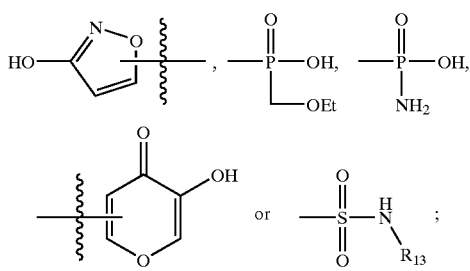

wherein $R_{13}$ is $C_1$–$C_6$ alkyl, $C_2$–$C_6$ alkenyl, $C_3$–$C_6$ cycloalkyl, —$CH_2$—($C_3$–$C_6$ cycloalkyl), $C_3$–$C_6$ cycloalkenyl, —$CH_2$—($C_3$–$C_6$ cycloalkenyl), optionally substituted aryl or heteroaryl groups or optionally substituted —$C_1$–$C_6$ alkyl-aryl or —$C_1$–$C_6$ alkyl-heteroaryl, with the aryl and heteroaryl groups and their optional substitution as defined herein.

As used herein, "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryl groups include phenyl, naphthyl and the like. As used herein, "heteroaryl" refers to a monocyclic or bicyclic aromatic group of from 1 to carbon atoms and 1 to 4 heteroatoms selected from oxygen, nitrogen and sulfur within at least one ring (if there is more than one ring). Such heteroaryl groups can have a single ring, such as pyridyl, pyrrolyl or furyl groups, or multiple condensed rings, such as indolyl, indolizinyl, benzofuranyl or benzothienyl groups. Preferred heteroaryls include pyridyl, pyrrolyl and furyl. It will be understood that the definitions of aryl and heteroaryl also refer to those portions of any aroyl or heteroaroyl groups described herein.

Unless otherwise limited by the definition for the aryl or heteroaryl groups herein, such groups can optionally be substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Substituents on the alkyl, alkenyl, alkynyl, thioalkoxy and alkoxy groups mentioned above include halogens, CN, OH, and amino groups. Preferred substituents on the aryl groups herein include alkyl, alkoxy, halo, cyano, nitro, trihalomethyl, and thioalkoxy.

Pharmaceutically acceptable salts of compounds of this invention containing a basic group, such as amino or alkylamino groups, can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from organic and inorganic bases, preferably alkali metal salts, for example, sodium, lithium, or potassium.

Other useful salt forms of these compounds include those formed with pharmaceutically acceptable inorganic and organic bases known in the art. Salt forms prepared using inorganic bases include hydroxides, carbonates or bicarbonates of the therapeutically acceptable alkali metals or alkaline earth methals, such as sodium potassium, magnesium, calcium and the like. Acceptable organic bases include amines, such as benzylzmine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Also useful are alkylene diamines containing up to 6 carbon atoms, such as hexamethylenediamine; cyclic saturated or unsaturated bases containing up to 6 carbon atoms, including pyrrolidine, peperidine, morpholine, piperazine and their N-alkyl and N-hydroxyalkyl derivatives, such as N-methyl-morpholine and N-(2-hyroxyethyl)-piperidine, or pyridine. Quaternary salts may also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-mehtyl-N-(2-hydroxyethyl)-morpholinium, or N,N-dimethyl-piperidinium salt forms. These salt forms may be prepared using the acidic compound(s) of Formula I and procedures known in the art.

The compounds of this invention may contain an asymmetric carbon atom or sulfoxide moiety and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

The compounds of the present invention are inhibitors of the serine protease inhibitor PAI-1, and are therefore useful in the treatment or prophylaxis of those processes which involve the production and/or action of PAI-1. Thus, the compounds of the invention are useful in the treatment or prevention of noninsulin dependent diabetes mellitus and cardiovascular disease caused by such condition, and prevention of thrombotic events associated with coronary artery and cerebrovascular disease. These compounds are also useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint replacement), and peripheral arterial occlusion. These compounds are also useful in treating stroke associated with or resulting from atrial fibrillation.

The compounds of the invention may also be used in the treatment of diseases associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be used in the treatment of malignancies, and diseases associated with neoangiogenesis (such as diabetic retinopathy).

The compounds in the invention may also be used in conjunction with and following processes or procedures involving maintaining blood vessel patency, including vascular surgery, vascular graft and stent patency, organ, tissue and cell implantation and transplantation.

The compounds of the invention may also be used in the treatment of Alzheimer's disease. This method may also be characterized as the inhibition of plasminogen activator by PAI-1 in a mammal, particularly a human, experiencing or subject to Alzhemier's disease. This method may also be characterized as a method of increasing or normalizing levels of plasmin concentration in a mammal, particularly those experiencing or subject to Alzheimer's disease.

The compounds of the invention may be used for the treatment of myelofibrosis with myeloid metaplasia by regulating stromal cell hyperplasia and increases in extracellular matrix proteins.

The compounds of the invention may also be used in conjunction with protease inhibitor-containing highly active antiretroviral therapy (HAART) for the treatment of diseases which orginate from fibrinolytic impairment and hypercoagulability of HIV-1 infected patients receiving such therapy.

The compounds of the invention may be used for the treatment of diabetic nephropathy and renal dialysis associated with nephropathy.

The compounds of the invention may be used to treat cancer, septicemia, obesity, insulin resistance, proliferative diseases such as psoriasis, improving coagulation homeostasis, cerebrovascular diseases, microvascular disease, hypertension, dementia, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, reducing the risk of undergoing a myocardial revascularization procedure, microvascular diseases such as nephropathy, neuropathy, retinopathy and nephrotic syndrome, hypertension, Type I and 2 diabetes and related diseases, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/or improving endothelial function, and all forms of cerebrovascular diseases.

The compounds of the invention may be used for the topical applications in wound healing for prevention of scarring.

The compounds in the invention can be used in the treatment of inflammatory diseases, septic shock and the vascular damage associated with infections and for the treatment of blood and blood products used in dialysis, blood storage in the fluid phase, especially ex vivo platelet aggregation. The compounds in the present invention may also be used in combination with prothrombolytic, fibrinolytic and anticoagulant agents. The present compounds may also be added to human plasma during the analysis of blood chemistry in hospital settings to determine the fibrinolytic capacity thereof.

This invention further comprises methods for treating, preventing, ameliorating or inhibiting each of the maladies mentioned herein in a mammal, preferably in a human, the method(s) each comprising administering to a mammal in need of such treatment, prevention, amelioration or inhibition a pharmaceutically or therapeutically effective amount of a compound of this invention, or a pharmaceutically acceptable salt or ester form thereof.

The compounds of the present invention may also be used to treat cancer including, but not limited to, breast and ovarian cancer, and as imaging agents for the identification of metastatic cancers.

It will be understood that a pharmaceutically or therapeutically effective amount of a compound herein refers to an amount of the compound in question which will sufficiently inhibit the serine protease inhibitor PAI-1 in the mammal in need thereof to a sufficient extent to provide a desirable improvement in the condition in question or provide sufficient inhibition of the serine protease inhibitor PAI-1 to prevent, inhibit or limit the onset of the physiological basis for the malady or condition in question.

A subset of the compounds of this invention are those of the Formula I:

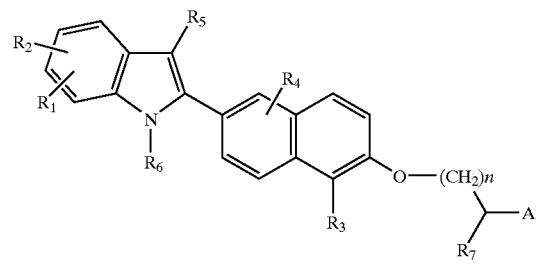

wherein $R_1$, $R_2$, $R_3$, $R_4$, $R_5$, $R_6$, $R_7$, A, n, and $R_8$ are as defined above, or a pharmaceutically acceptable salt thereof.

A further subset of the preferred compounds of this invention comprises those having the Formula I:

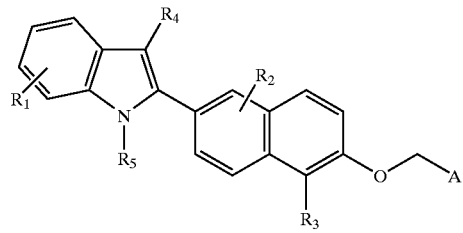

wherein:

$R_1$, $R_2$, and $R_3$, are each, independently, hydrogen, alkyl of 1–3 carbons, cycloalkyl of 3–5 carbons, alkanoyl of 1–3 carbons, halogen, hydroxy, aryl optionally substituted with from 1 to 3 groups selected from $R_6$, perfluoroalkyl of 1–3 carbons, alkoxy of 1–3 carbons, amino, alkylamino of 1–3 carbons, dialkylamino of 1–3 carbons per alkyl group, perfluoroalkoxy of 1–3 carbons;

$R_4$ is hydrogen, alkyl of 1–6 carbons, perfluoroalkyl of 1–6 carbons, aryl substituted with $R_6$, alkanoyl of 1–6 carbons, aroyl optionally substituted with from 1 to 3 groups selected from $R_6$;

$R_5$ is hydrogen, alkyl of 1–6 carbons, alkylaryl, benzyl optionally substituted with from 1 to 3 groups selected from $R_6$, alkanoyl of 1–6 carbons, aroyl substituted with $R_6$;

A is COOH or tetraazole;

$R_6$ is hydrogen, alkyl of 1–3 carbons, cycloalkyl of 3–5 carbons, —$CH_2$-cycloalkyl of 3–5 carbons, alkanoyl of 1–3 carbons, halogen, hydroxy, perfluoroalkyl of 1–3 carbons, alkoxy of 1–3 carbons, amino, alkylamino of 1–3 carbons, dialkylamino of 1–3 carbons, perfluoroalkoxy of 1–3 carbons;

or a pharmaceutically acceptable salt or ester form thereof.

Among the specifically preferred compounds of this invention are:

1-Benzyl-3-pentyl-2-[6-(1H-tetraazol-5-ylmethoxy)-2-naphthyl]-1H-indole or a pharmaceutically acceptable salt thereof;

6-(1-Benzyl-3-pentyl-1H-indol-2-yl)-1-bromo-2-naphthyl 1H-tetraazol-5-ylmethyl ether or 1-Benzyl-2-[5-bromo-6-(1H-tetraazol-5-ylmethoxy)-2-naphthyl]-3-pentyl-1H-indole or a pharmaceutically acceptable salt thereof;

1-Methyl-3-pentyl-2-[6-(1H-tetraazol-5-ylmethoxy)-2-naphthyl]-1H-indole or a pharmaceutically acceptable salt thereof;

2-[5-Bromo-6-(1H-tetraazol-5-ylmethoxy)-2-naphthyl]-1-methyl-3-pentyl-1H-indole or 1-Bromo-6-(1-methyl-3-pentyl-1H-indol-2-yl)-2-naphthyl 1H-tetraazol-5-ylmethyl ether or a pharmaceutically acceptable salt thereof;

1-Acetyl-3-pentyl-2-[6-(1H-tetraazol-5-ylmethoxy)-2-naphthyl]-1H-indole or a pharmaceutically acceptable salt thereof;

1-Acetyl-2-[5-bromo-6-(1H-tetraazol-5-ylmethoxy)-2-naphthyl]-3-pentyl-1H-indole or a pharmaceutically acceptable salt thereof;

3-Pentyl-2-[6-(1H-tetraazol-5-ylmethoxy)-2-naphthyl]-1-[2-(trifluoromethyl)benzyl]-1H-indole or a pharmaceutically acceptable salt thereof;

2-[5-Bromo-6-(1H-tetraazol-5-ylmethoxy)-2-naphthyl]-3-pentyl-1-[2-(trifluoromethyl)benzyl]-1H-indole or a pharmaceutically acceptable salt thereof;

1-(4-tert-Butylbenzyl)-3-pentyl-2-[6-(1H-tetraazol-5-ylmethoxy)-2-naphthyl]-1H-indole or a pharmaceutically acceptable salt thereof;

2-[5-Bromo-6-(1H-tetraazol-5-ylmethoxy)-2-naphthyl]-1-(4-tert-butylbenzyl)-3-pentyl-1H-indole or a pharmaceutically acceptable salt thereof;

{[1-Bromo-6-(1-methyl-3-pentyl-1H-indol-2-yl)-2-naphthyl]oxy}acetic acid or a pharmaceutically acceptable salt thereof.

This invention describes the composition and utility of Substituted Naphthyl Indole Derivatives of Formula I,

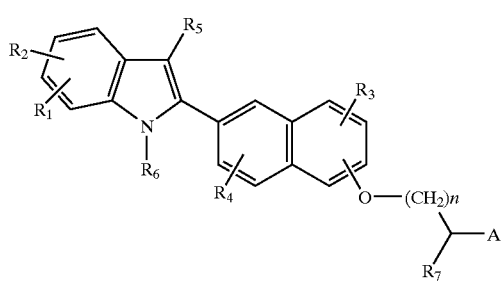

Wherein:

$R_1$, $R_2$, $R_3$, $R_4$ are independently one or more groups selected from hydrogen, alkyl, cycloalkyl, alkanoyl, halogen, hydroxy, aryl, substituted aryl, perfluoroalkyl, alkoxy, amino, alkylamino, dialkylamino, perfluoroalkoxy, $R_5$ is hydrogen, alkyl of 1–6 carbon atoms, perfluoroalkyl, aryl, substituted aryl, alkanoyl, aroyl, $R_6$ is a group selected from hydrogen, alkyl, alkylaryl, benzyl, substituted benzyl, alkanoyl, aroyl, $R_7$ is a group selected from hydrogen, alkyl, alkylaryl, aryl, substituted aryl, n is an integer of 0–6, A is COOH, or an acid mimic such as tetraazole, $SO_3H$, $PO_3H_2$, tetronic acid, etc.

Process of the Invention

The compounds of the present invention can be readily prepared according to the following reaction schemes or modification thereof using readily available starting materials, reagents and conventional synthetic procedures. It is also possible to make use of variants of these process steps, which in themselves are known to and well within the preparatory skill of the medicinal chemist. In the following reaction schemes, $R_1$, $R_2$, $R_3$, $R_4$, $R_5$, $R_6$, and $R_7$ are selected from the groups defined above.

In Scheme I, methoxy-naphthaldehydes (1) are converted to ketones 2 in a two step process. The first part utilizes Grignard chemistry to obtain an intermediate alcohol which is converted to the ketone via oxidation incorporating PCC or $MnO_2$. Compounds 2 were then subjected to Fisher type indole syntheses to generate the naphthyl indole core structures (3) using either an aryl hydrazine or an N-arylhydrazone. In the case where the hydrazone was used, varied substitution can be introduced into the indole framework; hydrazones can be generated using a recent procedure from JACS, S. Wagaw; B. H. Yang; S. L. Buchwald. *JACS*, 121, 1999, 10251–10263. At this point, the synthetic strategy can take one of two pathways, A and/or B. In Path A, naphthyl indoles 3 are N-alkylated ($R_6X$ equals alkyl halide such as methyl iodide) or N-acylated (($R_6$)$_2$O equals anhydride such as acetic anhydride) to afford intermediates such as compounds 4. These compounds are demethylated using boron tribromide to produce naphthols 5. Compounds 5 are O-alkylated using a variety of alkyl halides and cesium carbonate in acetone to generate the precursor compounds 8 to the target acids (9). The Z group on compounds 8 is a acid precursor such as a carboxylic ester or nitrile which can be converted to the carboxylic acids or tetraazoles (9) via hydrolysis or tetraazole formation respectively. An alternative route to acids 9 incorporating Path B also starts with naphthyl indoles 3. These indoles are first demethylated with boron tribromide to produce naphthols 6. Compounds 6 are O-alkylated using a variety of alkyl halides and cesium carbonate in acetone to generate indoles 7. These compounds are N-alkylated or N-acylated as in Path A to once again afford precursor compounds 8. At this point, Z groups are converted to the acids of compounds 9 as prevsiously described.

Scheme I
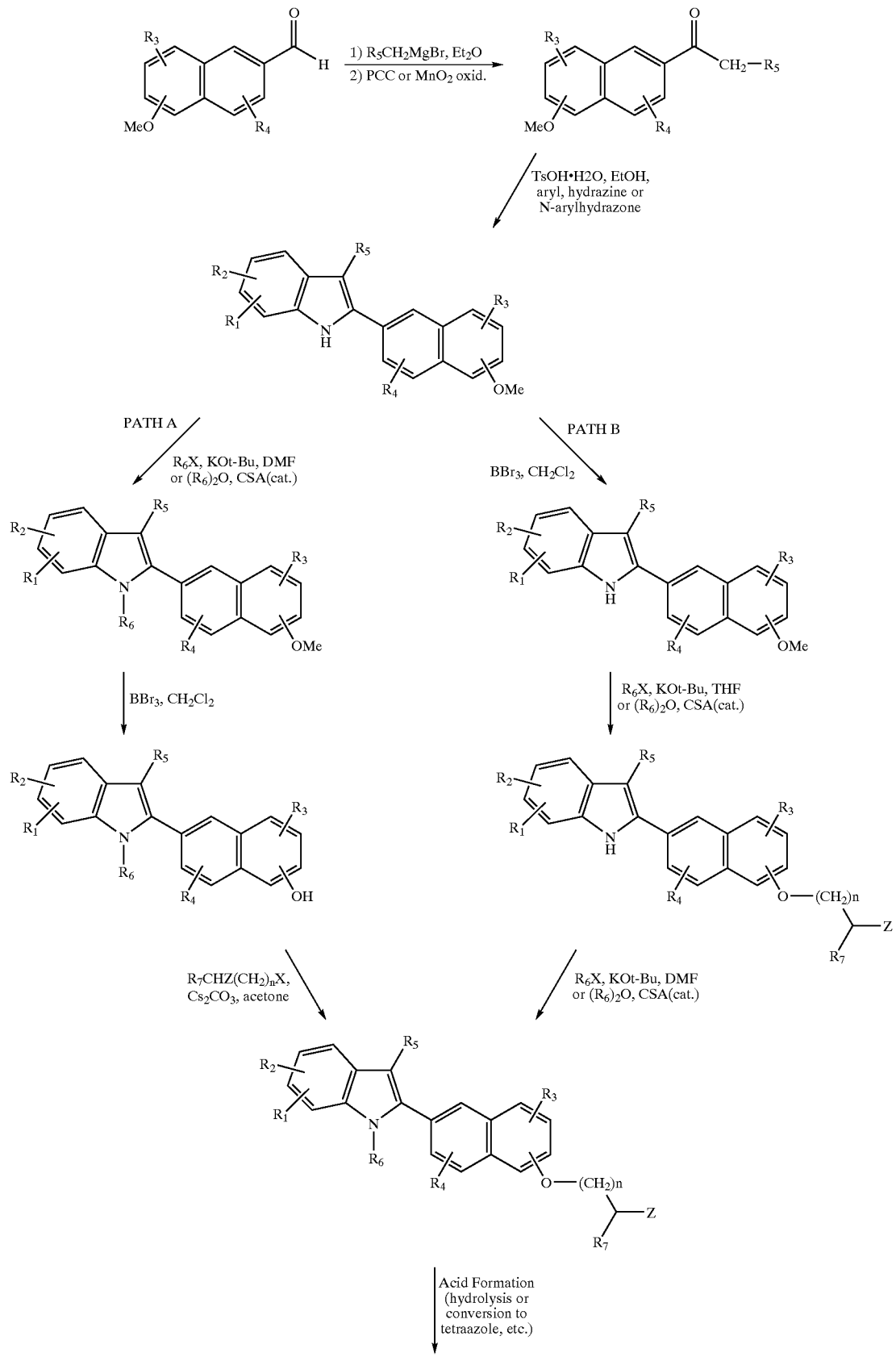

-continued

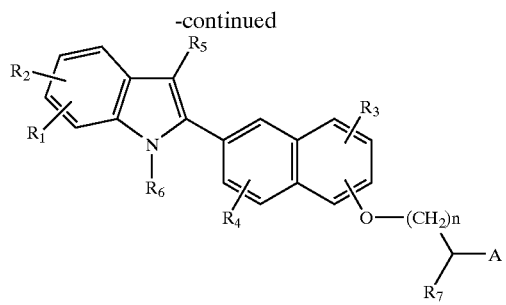

This invention also provides pharmaceutical compositions comprised of substituted naphthyl indole derivatives (I) either alone or in combination with excipients (i.e. pharmaceutically acceptable materials with no pharmacological effects). Such compositions for treating conditions resulting from fibrinolytic disorder such as deep vein thrombosis and coronary heart disease, pulmonary fibrosis, etc.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid, which is in admixture with the finely divided active ingredient. In tablets, the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of PAI-1 and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The ability of the compounds of this invention to inhibit plasminogen activator inhibitor-1 was established by the following experimental procedures:

Primary Screen for the PAI-1 Inhibition

Test compounds are dissolved in DMSO at a final concentration of 10 mM, then diluted 100× in physiologic buffer. The inhibitory assay is initiated by the addition of test compound (1–100 µM final concentration, maximum DMSO concentration of 0.2%) in a pH 6.6 buffer containing 140 nM recombinant human plasminogen activator inhibitor-1 (PAI-1; *Molecular Innovations*, Royal Oak, Mich.). Following a 1 hour incubation at room temperature, 70 nM of recombinant human tissue plasminogen activator (tPA) is added, and the combination of test compound, PAI-1 and tPA is incubated for an additional 30 minutes. Following the second incubation, Spectrozyme-tPA (*American Diagnostica*, Greenwich, Conn.), a chromogenic substrate for tPA, is added and absorbance read at 405 nm at 0 and 60 minutes. Relative PAI-1 inhibition is equal to the residual tPA activity in the presence of test compound and PAI-1. Control treatments include the complete inhibition of tPA by PAI-1 at the molar ratio employed (2:1), and the absence of any effect of the test compound on tPA alone.

Assay for Determining $IC_{50}$ of Inhibition of PAI-1

This assay is based upon the non-SDS dissociable interaction between tPA and active PAI-1. Assay plates are initially coated with human tPA (10 μg/ml). Test compounds are dissolved in DMSO at 10 mM, then diluted with physiologic buffer (pH 7.5) to a final concentration of 1–50 μM. Test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the test compound/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (*Molecular Innovations*, Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at $OD_{405\ nm}$. The quantitation of active PAI-1 bound to tPA at varying concentrations of test compound is used to determine the $IC_{50}$. Results are analyzed using a logarithmic best-fit equation. The assay sensitivity is 5 ng/ml of human PAI-1 as determined from a standard curve ranging from 0–100 ng/ml.

The compounds of the present invention inhibited Plasminogen Activator Inhibitor-1 as summarized in Table I:

TABLE I

| Compound of Example | $IC_{50}$ (μM) | % Inhibition @ 25 μM |
|---|---|---|
| 1 | 9.85[a] | |
| 2 | 8.8[b] | |
| 3 | 16.2[a] | |
| 4 | 17.4[b] | |
| 5 | 9.2[b] | |
| 6 | — | 16[a] |
| 7 | 5.22[a] | |
| 8 | — | 57[a] |
| 9 | 24.88[a] | |
| 10 | — | 60[a] |
| 11 | 10.73[a] | |

[a]The $IC_{50}$ was determined by the Antibody Assay described above.
[b]The $IC_{50}$ was determined by a modification of the Primary Screen for PAI-1 Inhibition.

EXPERIMENTAL EXAMPLES

The following provides the preparation of representative compounds of this invention.

Example 1

1-Benzyl-3-pentyl-2-[6-(1H-tetraazol-5-ylmethoxy)-2-naphthyl]-1H-indole

Step 1
1-(6-Methoxy-2-naphthyl)heptan-1-ol

To a 3-neck flask equipped with an overhead stirrer, dropping funnel and thermometer was added 6-methoxy-2-naphthaldehyde (70.760 g, 380 mmol) and $Et_2O$ (1400 mL). The stirred suspension under $N_2$ was cooled in an ice bath followed by the slow addition of hexylmagnesium bromide (228 mL of a 2 M solution in $Et_2O$) over 1 h. Temperature was kept below 12° C. After the addition, the reaction was stirred for 3 h at room temperature then cooled in an ice bath and slowly quenched w/saturated aq. $NH_4Cl$ (250 mL). After quenching, the ice bath was removed and the mixture was stirred for a half-hour then diluted with $H_2O$ (750 mL) to dissolve all solids. The layers were separated and the aqueous layer extracted with $Et_2O$ (3×200 mL). The combined organics were washed with water (3×200 mL), and brine (2×200 mL), dried over $Na_2SO_4$, filtered, rotovap'd and dried in vacuo to give the desired product as an off-white solid (101.1 g, 371.2 mmol, 98%) with mp 71–74° C. 15 g of crude alcohol was recrystallized from hexane to give the desired product as a white solid (11.7 g) with mp 71–73° C; $^1H$ NMR (DMSO-$d_6$) δ 0.82 (t, J=6.7 Hz, 3H), 1.15–1.38 (m, 8H), 1.58–1.71 (m, 2H) 3.85 (s, 3H), 4.58–4.64 (m, 1H), 5.14 (d, J=4.3 Hz, 1H), 7.12 (dd, J=2.6, 9.0 Hz, 1H), 7.26 (d, 2.4 Hz, 1H), 7.42 (dd, J=1.5, 8.4 Hz, 1H), 7.70 (s, 1H), 7.74 (d, J=8.6 Hz, 1H), 7.77 (d, J=8.9 Hz, 1H), IR (solid) 3280, 2920, 2860, 1610, 1270, 1170, 1040, and 860 $cm^{-1}$; mass spectrum [ESI], m/z 255 $(MH—H_2O)^+$;

Anal. Calcd. for $C_{18}H_{24}O_2$: C, 79.37; H, 8.88; N, 0.00, Found: C, 79.27; H, 8.94; N, −0.03.

Step 2
1-(6-Methoxy-2-naphthyl)heptan-1-one

To a stirred solution of the 1-(6-methoxy-2-naphthyl)heptan-1-ol (101.1 g, 371 mmol) in $CH_2Cl_2$ (1000 mL) under $N_2$ was added pyridinium chlorochromate (120.02 g, 556.74 mmol). The reaction was stirred for a total of 3 h and then poured onto an alumina column (2000 g, basic Brockman activity, 60–325 mesh). Column was eluted with $CH_2Cl_2$. Product was collected, filtered, rotovap'd and dried in vacuo to give the product as a white solid (81.5 g, 301.44 mmol, 81%) with mp 69–72° C. 177 mg of crude ketone was recrystallized from methanol to give the desired product as a white solid (105 mg) mp 70–72° C.; $^1H$ NMR (DMSO-$d_6$) δ 0.86 (m, 3H), 1.25–1.40 (m, 6H), 1.60–1.70 (m, 2H), 3.07 (t, J=7.3 Hz, 2H), 3.90 (s, 3H), 7.24 (d, J=9 Hz, 1H), 7.39 (s, 1H), 7.87 (d, J=8.7 Hz, 1H), 7.93 (d, J=8.7 Hz, 1H), 8.02 (d, J=8.9, 1H) 8.58 (s, 1H); IR (solid) 2910, 2870, 1660, 1630, 1470, and 1180 $cm^{-1}$; mass spectrum [EI], m/z 271 $(M+H)^+$;

Anal. Calcd. for $C_{18}H_{22}O_2$: C, 79.96; H, 8.20; N, 0.00, Found: C, 80.27; H, 8.16; N, 0.02.

Step 3
2-(6-Methoxy-2-naphthyl)-3-pentyl-1H-indole

To a stirred suspension of the 1-(6-methoxy-2-naphthyl)heptan-1-one (81.5 g, 301.44 mmol) in ethanol (2000 mL) under $N_2$ was added phenylhydrazine (35.857 g, 331.58 mmol) and p-toluene sulfonic acid monhydrate (120.41 g, 633.02 mmol). The mixture was refluxed. Warming gave a homogenous solution. (A modification of this Fisher indole reaction to incorporate varied substitution on the indole ring utilizes an N-arylhydrazone in place of the aryl hydrazine-details of hydrazone preparation in a recent JACS, S.Wagaw; B. H. Yang; S. L. Buchwald. *JACS*, 121, 1999, 10251–10263). After 92 h reflux, heating was stopped and the reaction mixture cooled and rotovap'd to a residue. The residue was partitioned between EtOAc (1700 mL) and 1 N HCl (500 mL). The layers were shaken, separated, and the organic layer washed with 1 N HCl (2×300 mL), sat. aq. $NaHCO_3$ (3×250 mL), $H_2O$ (3×250 mL), brine (2×250 mL), dried over $Na_2SO_4$, filtered, rotovap'd and dried in vacuo to give a dark viscous oil (106.2 g). The residue was triturated with hexane to give an off-white solid which was collected, rinsed and dried in vacuo to give the product as an off-white solid (95.9 g, 279.21 mmol, 93%) which dec. 93–96° C. 400 mg of the crude indole was recrystallized from hexane to give the product as a white solid (298 mg) with mp 95–97° C.; $^1H$ NMR (DMSO-$d_6$) δ 0.82 (t, J=7.0 Hz, 3H), 1.31 (m, 4H), 1.66 (m, 2H), 2.89 (t, J=7.6 Hz, 2H), 3.90 (s, 3H), 6.98–7.02 (m, 1H), 7.07–7.10 (m, 1H), 7.21 (dd, J=2.4, 8.9 Hz, 1H), 7.34–7.37 (m, 2H), 7.54 (d, J=7.94 Hz, 1H), 7.73 (dd, J=1.5, 8.6 Hz, 1H), 7.88 (d, J=9.00 Hz, 1H), 7.93 (d, J=8.55 Hz, 1H), 8.03 (s, 1H), 11.17 (s, 1H); IR (solid) 3350, 2960, 2920, 2840, 1600, 1200, 740, cm$^{-1}$; mass spectrum [ESI], m/z 344 (M+H)$^+$;

Anal. Calcd. for $C_{24}H_{25}NO$: C, 83.93; H, 7.34; N, 4.08, Found: C, 83.59; H, 7.51; N, 3.86.

Step 4

1-Benzyl-2-(6-methoxy-2-naphthyl)-3-pentyl-1H-indole

To a stirred solution of the 2-(6-methoxy-2-naphthyl)-3-pentyl-1H-indole (95.5 g, 278.04 mmol) in dry DMF (1000 mL) under N$_2$ at 0° C. (ice bath) was added k-t-butoxide (32.762 g, 291.95 mmol), portion-wise, over 20 minutes. After the addition of butoxide, the reaction mixture was stirred for 20 minutes followed by the addition of benzylbromide (50.110 g, 291.95 mmol) in one portion. An exotherm was noted and a precipitate formed. The bath was removed 10 minutes later. The reaction was stirred for ~5 h and then quenched w/conc. HOAc (0.05 eq, 13.902 mmol, 0.8 mL) and stirred overnight. The reaction mixture was rotovap'd to a residue which was partitioned between EtOAc (2 L) and 0.1 N HCl (600 mL). The layers were separated and the organic layer was washed with 0.1 N HCl (2×250 mL), H$_2$O (1×250 mL) and brine (2×250 mL), dried over Na$_2$SO$_4$, filtered, rotovap'd and dried to give a brown viscous residue (123.5 g). This residue was dissolved in hexane and flashed on silica (2000 g). The column was eluted with 1% EtOAc/hexane. The product was collected, filtered, rotovap'd and dried in vacuo to give the product as a viscous yellow oil (109.3 g, 252 mmol, 91%). 300 mg of the yellow oil was further purified by preparatory plate chromatography. The plates were eluted with 15% ethyl acetate/hexane. The product was collected, filtered, rotovap'd and dried in vacuo at room temperature to give the desired product as a waxy white solid, mp 76–80° C.; $^1$H NMR (DMSO-d$_6$) δ 0.72 (t, J=6.9 Hz, 3H), 1.10–1.20 (m, 4H), 1.51–1.60 (m, 2H), 2.67 (t, J=7.5 Hz, 2H), 3.89 (s, 3H), 5.30 (s, 2H), 6.81 (d, J=7.0 Hz, 2H), 7.04–7.22 (m, 6H), 7.34 (d, J=7.9 Hz, 1H), 7.36 (d, J=2.3 Hz, 1H), 7.41 (dd, J=1.4, 8.4 Hz, 1H), 7.60 (d, J=7.3 Hz, 1H), 7.80–7.84 (m, 3H), 7.87 (d, J=8.4 Hz, 1H); IR (solid) 2910, 1605, 1460, 1200, and 740 cm$^{-1}$; mass spectrum [ESI], m/z 434 (M+H)$^+$;

Anal. Calcd. for $C_{31}H_{31}NO$: C, 85.87; H, 7.21; N, 3.23, Found: C, 85.43; H, 7.31; N, 3.14.

Step 5

6-(1-Benzyl-3-pentyl-1H-indol-2-yl)-2-naphthol

To a stirred solution of the 1-benzyl-2-(6-methoxy-2-naphthyl)-3-pentyl-1H-indole (109.0 g, 251 mmol) in CH$_2$Cl$_2$ (1000 mL) under N$_2$ at −78° C. was added BBr$_3$ (1M in CH$_2$Cl$_2$, 302 mL), dropwise, over 1.5 h. After the addition, the reaction was warmed to 0° C. and stirred for 2.5 h then warmed to rt. After a total of 5 h the reaction mixture was cooled to 0° C. and quenched with water (250 mL). The mixture was stirred overnight then rotovap'd to a residue. The residue was partitioned between EtOAc (1500 mL) and H$_2$O (500 mL). The layers were shaken, separated, and the organic layer was washed with H$_2$O (2×250 mL), brine (2×250 mL), dried over Na$_2$SO$_4$, filtered, rotovap'd and dried in vacuo to give a viscous black goo (114 g). The residue was dissolved in CHCl$_3$ and flashed on silica (2000 g). The column was eluted with hexane and 8% EtOAc/ Hexane. The product was collected, filtered, rotovap'd and the residue triturated with hexane then dried to give the product as an off-white solid (89.2 g, 213 mmol, 85%) with mp 96–100° C. 400 mg of the crude solid was recrystallized from hexane to give desired product as an off-white solid (311 mg) with mp 97–100° C.; $^1$H NMR (DMSO-d$_6$) δ 0.73 (t, J=6.7 Hz, 3H), 1.10–1.20 (m, 4H), 1.51–1.60 (m, 2H), 2.67 (t, J=7.3 Hz, 3H), 5.29 (s, 2H), 6.82 (d, J=7.2 Hz, 2H), 7.04–7.20 (m, 7H), 7.30–7.35 (m, 2H), 7.59 (d, J=7.8 Hz, 1H), 7.73–7.78 (m, 3H); IR (solid) 3380, 2920, 1610, 1200, 740 cm$^{-1}$; mass spectrum [ES], m/z 420 (M+H)$^+$;

Anal. Calcd. for $C_{30}H_{29}NO$: C, 85.88; H, 6.97; N, 3.34, Found: C, 85.85; H, 7.10; N, 3.20.

Step 6

{[6-(1-Benzyl-3-pentyl-1H-indol-2-yl)-2-naphthyl]oxy}acetonitrile

To a solution of 6-(1-benzyl-3-pentyl-1H-indol-2-yl)-2-naphthol (19.245 g, 45.868 mmol) in acetone (200 mL) at rt under N$_2$ was added Cs$_2$CO$_3$ (16.439 g, 50.455 mmol) followed by the bromide (6.052 g, 50.455 mmol). After stirring for 4.5 h, the reaction was rotovap'd to a residue. The residue was partitioned between EtOAc (350 mL) and H$_2$O (150 mL). The layers were shaken, separated, and the organic layer washed with H$_2$O (2×80 mL), brine (2×80 mL), dried over Na$_2$SO$_4$, filtered, rotovap'd, and dried to give a viscous brown oil (20.664 g). The residue was taken in CHCl$_3$ and flashed on silica (435 g). The column was eluted with hexane and 8% EtOAc/Hex. The product was collected, filtered, rotovap'd, triturated with hexane and dried to give the product as a white solid (18.78 g, 40.95 mmol, 89%) with mp 111–113° C. 400 mg of the crude product was recrystallized from MeOH to give the desired product as a white solid (0.362 g) with mp 109–112° C.; $^1$H NMR (DMSO-d$_6$) δ 0.72 (t, J=6.9 Hz, 3H), 1.10–1.20 (m, 4H), 1.52–1.59 (m, 2H), 2.68 (t, J=7.5 Hz, 2H), 5.31 (s, 4H), 6.81 (d, J=7.2 Hz, 2H), 7.05–7.19 (m, 5H), 7.31 (dd, J=2.6, 9.0 Hz, 1H), 7.36 (d, J=8.1 Hz, 1H), 7.47 (dd, J=1.4, 8.2 Hz, 1H) 7.56 (d, J=2.4 Hz, 1H), 7.6 (d, J=7.6 Hz, 1H) 7.88–7.94 (m, 3H); IR (solid) 2940, 1610, 1460, and 1200 cm$^{-1}$; mass spectrum [ESI], m/z 459 (M+H)$^+$;

Anal. Calcd. for $C_{32}H_{30}N_2O$: C, 83.81; H, 6.59; N, 6.11, Found: C, 83.93; H, 6.60; N, 6.05.

Step 7

1-Benzyl-3-pentyl-2-[6-(1H-tetraazol-5-ylmethoxy)-2-naphthyl]-1H-indole

To a stirred solution of the {[6-(1-benzyl-3-pentyl-1H-indol-2-yl)-2-naphthyl]oxy}acetonitrile (87.0 g, 189.71 mmol) in DMF (900 mL) under N$_2$ was added NaN$_3$ (61.665 g, 948.54 mmol) and NH$_4$Cl (50.737 g, 948.54 mmol). The reaction was heated between 95–100° C. for 1.33 h then cooled. The reaction mixture was rotovap'd to a residue and the residue partitioned between EtOAc (2000 mL) and 1 N HCl (600 mL). The layers were shaken, separated, and the organic layer washed with 1 N HCl (2×300 mL), H$_2$O (3×300 mL), and brine (2×300 mL), dried over Na$_2$SO$_4$, filtered, rotovap'd and triturated with hexane to give an off-white solid (97.5 g). The product was purified by refluxing the solid in diethyl ether (2000 mL), concentrating to about a liter and cooling. The solids were collected and dried in vacuo to give the product as a white solid (77.4 g, 154.3 mmol, 81%) with dec. 111–114° C.; $^1$H NMR (DMSO-d$_6$) δ 0.72 (t, J=6.9 Hz, 3H) 1.10–1.20 (m, 4H), 1.50–1.60 (m, 2H), 2.67 (t, J=7.8 Hz, 2H), 5.30 (s, 2H), 5.62 (s, 2H), 6.81 (d, J=7.3 Hz, 2H), 7.02–7.20 (m, 5H), 7.30 (dd, J=2.4, 9.0 Hz, 1H), 7.35 (d, J=7.9 Hz, 1H), 7.44 (dd, J=1.5, 8.2 Hz, 1H), 7.55 (d, J=2.3 Hz, 1H), 7.60 (d, J=7.6 Hz, 1H), 7.84–7.90 (m, 3H) 16.9 (s, 1H); IR (solid) 2920, 2850, 1610, 1390, 1200, 860, and 750, cm$^1$; mass spectrum [ESI], m/z 502 (M+H)$^+$;

Anal. Calcd. for $C_{32}H_{31}N_5O$: C, 76.62; H, 6.23; N, 13.96, Found: C, 76.43; H, 6.12; N, 14.19.

Example 2

6-(1-Benzyl-3-pentyl-1H-indol-2-yl)-1-bromo-2-naphthyl 1H-tetraazol-5-ylmethyl ether or 1-Benzyl-2-[5-bromo-6-(1H-tetraazol-5-ylmethoxy)-2-naphthyl]-3-pentyl-1H-indole Step 1

2-(6-Hydroxy-2-naphthyl)-3-pentyl-1H-indole

To a stirred solution of 2-(6-methoxy-2-naphthyl)-3-pentyl-1H-indole (0.915 g, 2.66 mmol) in $CH_2Cl_2$ (30 mL) cooled to −78° C. was added $BBr_3$ (9.86 mL, 1.0 M in $CH_2Cl_2$, 9.86 mmol) dropwise. The reaction was stirred at this temperature for 0.5 h and then warmed to rt for 2 h. The reaction mixture was quenched with MeOH (~5 mL) followed by dilution with $H_2O$ (20 mL) and EtOAc (200 mL). The organic layer was washed with brine (20 mL) and then dried ($Na_2SO_4$). After concentration, the residue was purified by the Biotage Flash 40 apparatus (10 to 20% EtOAc:petroleum ether gradient) to afford the product (0.677 g, 77%) as a foamy solid; $^1$H NMR (DMSO-$d_6$) δ 0.83 (t, J=7.3 Hz, 3H), 1.23–1.42 (m, 4H), 1.58–1.76 (m, 2H), 2.89 (t, J=8.2 Hz, 2H), 7.00 (t, J=8.2 Hz, 1H), 7.06–7.19 (m, 3H), 7.35 (d, J=8.2 Hz, 1H), 7.53 (d, J=8.2, 1H), 7.67 (d, J=9.1 Hz, 1H), 7.74–7.88 (m, 2H), 7.98 (s, 1H), 9.83 (s, 1H), 11.14 (s, 1H); mass spectrum [(+) ESI], m/z 330 (M+H)$^+$ and [(−) ESI], m/z 328 (M−H)$^−$.

Step 2

2-(5-Bromo-6-hydroxy-2-naphthyl)-3-pentyl-1H-indole

To a stirred solution of 2-(6-hydroxy-2-naphthyl)-3-pentyl-1H-indole (1.27 g, 3.85 mmol) in HOAc (25 mL) at 0° C. was added KOAc (0.453 g, 4.62 mmol). The reaction was stirred at this temperature for 10 min., and then a solution of $Br_2$ (0.218 mL, 4.24 mmol) in HOAc (5 mL) was added dropwise to it over a period of ~10 min. The reaction mixture was allowed to warm to rt and stirred for 4 h. The reaction mixture was then diluted with $H_2O$ (50 mL) and extracted with EtOAc (200 mL). The organic layer was washed with brine (20 mL) and then dried ($Na_2SO_4$). After concentration, the residue was purified by the Biotage Flash 40 apparatus (10 to 30% EtOAc:petroleum ether gradient) to afford the product (0.782 g, 50%) as a solid (inseparable mixture of mono- and di-bromo-substituted analogs which were separated in the next step); monobrominated compound: mass spectrum [(−) ESI], m/z 406/408 (M−H)$^−$ and dibrominated analog: mass spectrum [(−) ESI], m/z 486 (M−H)$^−$.

Step 3

{[1-Bromo-6-(3-pentyl-1H-indol-2-yl)-2-naphthyl]oxy}acetonitrile and {[1-Bromo-6-(5-bromo-3-pentyl-1H-indol-2-yl)-2-naphthyl]oxy}acetonitrile To a stirred solution of 2-(5-bromo-6-hydroxy-2-naphthyl)-3-pentyl-1H-indole (0.740 g, 1.81 mmol) in acetone (20 mL) at rt was added $Cs_2CO_3$ (1.30 g, 3.98 mmol) followed by bromoacetonitrile (0.139 mL, 1.99 mmol) dropwise. The reaction was stirred at this temperature for 6 h and then diluted with EtOAc (200 mL). The organic layer was washed with $H_2O$ (20 mL) and brine (20 mL) and then dried ($Na_2SO_4$). After concentration, the residue was purified by the Biotage Flash 40 apparatus (20% EtOAc:petroleum ether) to afford the product (0.315 g, 39%) as a foamy solid as well as the dibrominated analog (0.141 g, 15%); monobrominated compound. $^1$H NMR (DMSO-$d_6$) δ 0.82 (t, J=7.3 Hz, 3H), 1.22–1.42 (m, 4H), 1.60–1.74 (m, 2H), 2.93 (t, J=8.2 Hz, 2H), 5.46 (s, 2H), 7.02 (t, J=7.3 Hz, 1H), 7.13 (t, J=7.3 Hz, 1H), 7.39 (d, J=8.2 Hz, 1H), 7.58 (d, J=8.2 Hz, 1H), 7.67 (d, J=9.1 Hz, 1H), 7.97 (d, J=9.1 Hz, 1H), 8.10–8.28 (m, 3H), 11.31 (s, 1H); mass spectrum [(−) ESI], m/z 445/447 (M−H)$^−$ and dibrominated analog: $^1$H NMR (DMSO-$d_6$) δ 0.81 (t, J=7.7 Hz, 3H), 1.21–1.40 (m, 4H), 1.57–1.73 (m, 2H), 2.92 (t, J=8.7 Hz, 2H), 5.46 (s, 2H), 7.16 (d, J=8.7 Hz, 1H), 7.51–7.59 (m, 2H), 7.69 (d, J=8.7 Hz, 1H), 7.95 (d, J=9.7 Hz, 1H), 8.12–8.31 (m, 3H), 11.50 (s, 1H); mass spectrum [(−) ESI], m/z 525 (M−H)$^−$.

Step 4

{[6-(1-Benzyl-3-pentyl-1H-indol-2-yl)-1-bromo-2-naphthyl]oxy}acetonitrile

To a stirred solution of {[1-bromo-6-(3-pentyl-1H-indol-2-yl)-2-naphthyl]oxy}acetonitrile (0.135 g, 0.257 mmol) in THF (5 mL) at 0° C. was added KOt-Bu (0.032 g, 0.283 mmol) followed by BnBr (0.019 mL, 0.308 mmol). The reaction was warmed to rt and let stir for 24 h. After this time, the reaction mixture was quenched with 1 N HCl (~2 mL). The resulting solution was diluted with EtOAc (100 mL). The organic layer was washed with 1 N HCl (10 mL), sat. aq. $NaHCO_3$ (10 mL), and brine (10 mL) and then dried ($MgSO_4$). After concentration, the residue was purified by preparatory plate chromatography (20% EtOAc:petroleum ether) to afford the product (0.105 g, 56%) as a solid; $^1$H NMR (DMSO-$d_6$) δ 0.73 (t, J=7.4 Hz, 3H), 1.09–1.23 (m, 4H), 1.47–1.63 (m, 2H), 2.70 (t, J=7.7 Hz, 2H), 5.34 (s, 2H), 5.46 (s, 2H), 6.81 (d, J=7.4 Hz, 2H), 7.04–7.23 (m, 5H), 7.41 (d, J=8.1 Hz, 1H), 7.62–7.73 (m, 3H), 8.02 (s, 1H), 8.12 (d, J=9.2 Hz, 1H), 8.20 (d, J=9.2 Hz, 1H); mass spectrum [(+) ESI], m/z 537/539 (M+H)$^+$.

Step 5

6-(1-Benzyl-3-pentyl-1H-indol-2-yl)-1-bromo-2-naphthyl 1H-tetraazol-5-ylmethyl ether or 1-Benzyl-2-[5-bromo-6-(1H-tetraazol-5-ylmethoxy)-2-naphthyl]-3-pentyl-1H-indole To a stirred solution of {[6-(1-benzyl-3-pentyl-1H-indol-2-yl)-1-bromo-2-naphthyl]oxy}actonitrile (0.101 g, 0.188 mmol) in DMF (7 mL) at rt was added $NaN_3$ (0.061 g, 0.940 mmol) followed by $NH_4Cl$ (0.050 g, 0.940 mmol). The reaction was heated to 100° C. for 2 h. After this time, it was concentrated and diluted with 2 N HCl (~5 mL). This mixture was stirred at rt for 2 h and then extracted with EtOAc (100 mL). The organic layer was washed with 2 N HCl (10 mL) and brine (10 mL) and then dried ($MgSO_4$). The resulting solution was concentrated to afford the product (0.065 g, 60%) as a yellow foam, mp>70° C. (decomp.); $^1$H NMR (DMSO-$d_6$) δ 0.72 (t, J=6.9 Hz, 3H), 1.09–1.20 (m, 4H), 1.50–1.59 (m, 2H), 2.68 (t, J=7.3 Hz, 2H), 5.32 (s, 2H), 5.71 (s, 2H), 6.77–6.81 (m, 2H), 7.07 (t, J=7.6 Hz, 1H), 7.10–7.18 (m, 4H), 7.38 (d, J=8.1 Hz, 1H), 7.58–7.64 (m, 2H), 7.70 (d, J=9.0 Hz, 1H), 7.97 (s, 1H), 8.03 (d, J=9.2 Hz, 1H), 8.15 (d, J=8.9 Hz, 1H), 15.90–17.70 (bs, 1H); IR (neat) 3030, 2950, 2925, 2855, 1600, 1565, 1495, 1475, 1465, 1455, 1405, 1330, 1270, 1745, 1195, 1145, 1050, 1030, 1020, 975, 920, 895, 830, 800, 740, 700, and 675 cm$^{-1}$; mass spectrum [(−) ESI], m/z 578 (M−H)$^−$;

Anal. Calcd. for $C_{32}H_{30}BrN_5O\cdot1.5H_2O$: C, 63.26; H, 5.47; N, 11.53, Found: C, 63.16; H, 5.11; N, 11.33.

Example 3

1-Methyl-3-pentyl-2-[6-(1H-tetraazol-5-ylmethoxy)-2-naphthyl]-1H-indole

Step 1

{[6-(3-Pentyl-1H-indol-2-yl)-2-naphthyl]oxy}acetonitrile

The title compound was prepared as a solid (0.633 g, 84%) from 2-(6-hydroxy-2-naphthyl)-3-pentyl-1H-indole using the procedure from step 3 of Example 2; $^1$H NMR (DMSO-$d_6$) δ 0.83 (t, J=7.5 Hz, 3H), 1.24–1.42 (m, 4H), 1.60–1.75 (m, 2H), 2.93 (t, J=8.4 Hz, 2H), 5.33 (s, 2H), 7.02 (t, J=8.4 Hz, 1H), 7.11 (t, J=8.4 Hz, 1H), 7.28–7.41 (m, 2H), 7.52–7.62 (m, 2H), 7.80 (d, J=9.3 Hz, 1H), 7.99 (d, J=9.3

Hz, 2H), 8.13 (s, 1H), 11.23 (s, 1H); mass spectrum [(−) ESI], m/z 367 (M−H)⁻.

Step 2
{[6-(1-Methyl-3-pentyl-1H-indol-2-yl)-2-naphthyl]oxy}acetonitrile

The title compound was prepared as a solid (0.412 g, 83%) from {[6-(3-pentyl-1H-indol-2-yl)-2-naphthyl]oxy}acetonitrile using MeI and the procedure from step 4 of Example 2; $^1$H NMR (DMSO-d$_6$) δ 0.74 (t, J=7.5 Hz, 3H), 1.07–1.27 (m, 4H), 1.47–1.65 (m, 2H), 2.68 (t, J=8.3 Hz, 2H), 3.59 (s, 3H), 5.34 (s, 2H), 7.08 (t, J=8.3 Hz, 1H), 7.19 (t, J=8.3 Hz, 1H), 7.34 (dd, J=1.5, 9.0 Hz, 1H), 7.48 (d, J=9.0 Hz, 1H), 7.53–7.66 (m, 3H), 7.92–8.08 (m, 3H); mass spectrum [(+) ESI], m/z 383 (M+H)⁺.

Step 3
1-Methyl-3-pentyl-2-[6-(1H-tetraazol-5-ylmethoxy)-2-naphthyl]-1H-indole

The title compound was prepared as a lt. tan solid (0.311 g, 74%) from {[6-(1-methyl-3-pentyl-1H-indole-2-yl)-2-naphthyl]oxy}acetonitrile using the procedure from step 5 of Example 2, mp 120–122° C.; $^1$H NMR (DMSO-d$_6$) δ 0.73 (t, J=6.9 Hz, 3H), 1.09–1.24 (m, 4H), 1.48–1.60 (m, 2H), 2.66 (t, J=7.2 Hz, 2H), 3.58 (s, 3H), 5.65 (s, 2H), 7.06 (t, J=7.6 Hz, 1H), 7.18 (t, J=7.4 Hz, 1H), 7.33 (dd, J=2.5, 8.9 Hz, 1H), 7.45 (d, J=8.1 Hz, 1H), 7.51–7.62 (m, 3H), 7.91–8.01 (m, 3H), 15.08–17.10 (bs, 1H); IR (neat) 3130, 3040, 2950, 2930, 2890, 2860, 2795, 1625, 1605, 1565, 1500, 1485, 1470, 1440, 1430, 1390, 1360, 1340, 1325, 1265, 1230, 1220, 1200, 1170, 1135, 1100, 1045, 1035, 1015, 965, 930, 905, 845, 830, 785, 740, 705, and 680 cm⁻¹; mass spectrum [(+) APCI], m/z 426 (M+H)⁺;

Anal. Calcd. for C$_{26}$H$_{27}$N$_5$O: C, 73.39; H, 6.40; N, 16.46, Found: C, 73.08; H, 6.57; N, 16.45.

Example 4

2-[5-Bromo-6-(1H-tetraazol-5-ylmethoxy)-2-naphthyl]-1-methyl-3-pentyl-1H-indole or 1-Bromo-6-(1-methyl-3-pentyl-1H-indol-2-yl)-2-naphthyl 1H-tetraazol-5-ylmethyl ether Step 1
{[6-(1-Methyl-3-pentyl-1H-indol-2-yl)-1-bromo-2-naphthyl]oxy}acetonitrile The title compound was prepared as a solid (0.111 g, 69%) from {[1-bromo-6-(3-pentyl-1H-indol-2-yl)-2-naphthyl]oxy}acetonitrile using MeI and the procedure from step 4 of Example 2; $^1$H NMR (DMSO-d$_6$) δ 0.73 (t, J=7.4 Hz, 3H), 1.08–1.26 (m, 4H), 1.47–1.62 (m, 2H), 2.69 (t, J=8.2 Hz, 2H), 3.61 (s, 3H), 5.48 (s, 2H), 7.09 (t, J=7.4 Hz, 1H), 7.21 (t, J=7.4 Hz, 1H), 7.49 (d, J=8.2 Hz, 1H), 7.61 (d, J=8.2 Hz, 1H), 7.68–7.80 (m, 2H), 8.08 (s, 1H), 8.22 (d, J=8.9 Hz, 1H), 8.27 (d, J=8.9 Hz, 1H); mass spectrum [(+) ESI], m/z 461/463 (M+H)⁺.

Step 2
2-[5-Bromo-6-(1H-tetraazol-5-ylmethoxy)-2-naphthyl]-1-methyl-3-pentyl-1H-indole or 1-Bromo-6-(1-methyl-3-pentyl-1H-indol-2-yl)-2-naphthyl 1H-tetraazol-5-ylmethyl ether The title compound was prepared as a lt. brown solid (0.070 g, 61%) from {[6-(1-methyl-3-pentyl-1H-indole-2-yl)-1-bromo-2-naphthyl]oxy}acetonitrile using the procedure from step 5 of Example 2, mp>125° C. (decomp.); $^1$H NMR (DMSO-d$_6$) δ 0.73 (t, J=6.9 Hz, 3H), 1.11–1.21 (m, 4H), 1.50–1.57 (m, 2H), 2.66 (t, J=7.5 Hz, 2H), 3.59 (s, 3H), 5.60 (s, 2H), 7.07 (t, J=7.2 Hz, 1H), 7.19 (t, J=7.3 Hz, 1H), 7.46 (d, J=8.2 Hz, 1H), 7.58 (d, J=7.9 Hz, 1H), 7.68 (d, J=8.7 Hz, 1H), 7.81 (d, J=9.0 Hz, 1H), 8.01 (s, 1H), 8.09 (d, J=9.0 Hz, 1H), 8.20 (d, J=8.7 Hz, 1H), 15.95–17.95 (bs, 1H); IR (neat) 3050, 2950, 2920, 2855, 1600, 1565, 1475, 1470, 1405, 1365, 1330, 1270, 1245, 1185, 1160, 1150, 1135, 1100, 1055, 1020, 975, 915, 895, 825, 800, 765, 740, 700, and 670 cm⁻¹; mass spectrum [(−) ESI], m/z 502 (M−H)⁻;

Anal. Calcd. for C$_{26}$H$_{26}$BrN$_5$O.1.25H$_2$O: C, 59.26; H, 5.45; N, 13.29, Found: C, 58.89; H, 5.07; N, 12.83.

Example 5

1-Acetyl-3-pentyl-2-[6-(1H-tetraazol-5-ylmethoxy)-2-naphthyl]-1H-indole

Step 1
{[6-(1-Acetyl-3-pentyl-1H-indol-2-yl)-2-naphthyl]oxy}acetonitrile

To a stirred solution of {[6-(3-pentyl-1H-indol-2-yl)-2-naphthyl]oxy}acetonitrile (0.300 g, 0.814 mmol) in Ac$_2$O (3 mL, 3.18 mmol) at rt was added a catalytic amount of CSA (0.019 g, 0.0814 mmol). The reaction was heated to 70° C. for 18 h, and by TLC the reaction was about one half complete. Another 19 mg of CSA added and kept at 70° C. for an additional 24 h. After this time, the reaction mixture was quenched with 1 N HCl (~2 mL). The resulting solution was extracted with EtOAc (100 mL). The organic layer was washed with 1 N HCl (10 mL), sat. aq. NaHCO$_3$ (10 mL), and brine (10 mL) and then dried (MgSO$_4$). After concentration, the residue was purified by the Biotage Flash 40 apparatus (10 to 20% EtOAc:petroleum ether gradient) to afford the product (0.164 g, 49%) as a solid; $^1$H NMR (DMSO-d$_6$) δ 0.73 (t, J=7.2 Hz, 3H), 1.03–1.23 (m, 4H), 1.47–1.61 (m, 2H), 1.92 (s, 3H), 3.24–3.42 (m, 2H), 5.34 (s, 2H), 7.27–7.43 (m, 3H), 7.52–7.70 (m, 3H), 7.94–8.08 (m, 3H), 8.33 (d, J=8.8 Hz, 1H); mass spectrum [(+) ESI], m/z 411 (M+H)⁺, 433 (M+Na)⁺.

Step 2
1-Acetyl-3-pentyl-2-[6-(1H-tetraazol-5-ylmethoxy)-2-naphthyl]-1H-indole

The title compound was prepared as a yellow foamy solid (0.097 g, 56%) from {[6-(1-acetyl-3-pentyl-1H-indol-2-yl)-2-naphthyl]oxy}acetonitrile using the procedure from step 5 of Example 2, mp>95° C. (decomp.); $^1$H NMR (DMSO-d$_6$) δ 0.71 (t, J=7.0 Hz, 3H), 1.08–1.19 (m, 4H), 1.47–1.56 (m, 2H), 1.90 (s, 3H, 2.51 (t, J=7.6 Hz, 2H), 5.55 (s, 2H), 7.29–7.38 (m, 3H), 7.52 (dd, J=1.5, 8.4 Hz, 1H), 7.60 (d, J=2.1 Hz, 1H), 7.63 (d, J=7.2 Hz, 1H), 7.92–7.98 (m, 3H), 8.31 (d, J=7.8 Hz, 1H), 14.75–17.75 (bs, 1H); IR (neat) 3050, 2955, 2925, 2860, 1695, 1630, 1610, 1575, 1500, 1475, 1455, 1370, 1335, 1305, 1265, 1240, 1200, 1170, 1155, 1130, 1100, 1060, 1025, 950, 920, 900, 865, 810, 750, 700, and 675 cm⁻¹; mass spectrum [(+) ESI], m/z 454 (M+H)⁺;

Anal. Calcd. for C$_{27}$H$_{27}$N$_5$O$_2$.2.0H$_2$O: C, 66.24; H, 6.38; N, 14.30, Found: C, 65.85; H, 5.76; N, 13.53.

Example 6

1-Acetyl-2-[5-bromo-6-(1H-tetraazol-5-ylmethoxy)-2-naphthyl]-3-pentyl-1H-indole

Step 1
{[6-(1-Acetyl-3-pentyl-1H-indol-2-yl)-1-bromo-2-naphthyl]oxy}acetonitrile The title compound was prepared as a solid (0.093 g, 31%) from {[1-bromo-6-(3-pentyl-1H-indol-2-yl)-2-naphthyl]oxy}acetonitrile using the procedure from step 1 of Example 5; $^1$H NMR (DMSO-d$_6$) δ 0.72 (t, J=7.2 Hz, 3H), 1.07–1.21 (m, 4H), 1.48–1.59 (m, 2H), 1.97 (s, 3H), 2.42–2.57 (m, 2H), 5.48 (s, 2H), 7.27–7.46 (m, 2H), 7.63–7.80 (m, 3H), 8.13 (s, 1H), 8.15–8.36 (m, 3H); mass spectrum [(+) ESI], m/z 489/491 (M+H)⁺, 511/513 (M+Na)⁺.

Step 2

1-Acetyl-2-[5-bromo-6-(1H-tetraazol-5-yl methoxy)-2-naphthyl]-3-pentyl-1H-indole The title compound was prepared as a light yellow foam (0.028 g, 29%) from {[6-(1-acetyl-3-pentyl-1H-indol-2-yl)-1-bromo-2-naphthyl]oxy}acetonitrile using the procedure from step 5 of Example 2, mp>79° C. (decomp.); $^1$H NMR (DMSO-d$_6$) δ 0.71 (t, J=7.0 Hz, 3H), 1.08–1.18 (m, 4H), 1.48–1.56 (m, 2H), 1.95 (s, 3H), 2.48–2.56 (m, 2H), 5.73 (s, 2H), 7.32 (td, J=1.1, 7.5 Hz, 1H), 7.37 (td, J=1.2, 7.3 Hz, 1H), 7.65 (d, J=7.8 Hz, 1H), 7.70 (dd, J=1.7, 8.7 Hz, 1H), 7.74 (d, J=9.0 Hz, 1H), 8.08 (d, J=1.5 Hz, 1H), 8.12 (d, J=9.0 Hz, 1H), 8.20 (d, J=8.7 Hz, 1H), 8.30 (d, J=7.8 Hz, 1H), 14.75–17.75 (bs, 1H); IR (neat) 3140, 3050, 2950, 2920, 2860, 2630, 1695, 1630, 1600, 1570, 1475, 1450, 1370, 1340, 1300, 1270, 1245, 1205, 1195, 1140, 1095, 1045, 1020, 980, 915, 900, 875, 830, 805, 750, 700, and 670 cm$^{-1}$; mass spectrum [(+) ESI], n/z 532/534 (M+H)$^+$;

Anal. Calcd. for C$_{27}$H$_{26}$BrN$_5$O$_2$·1.0H$_2$O: C, 58.92; H, 5.13; N, 12.72, Found: C, 58.74; H, 4.76; N, 12.21.

Example 7

3-Pentyl-2-[6-(1H-tetraazol-5-ylmethoxy)-2-naphthyl]-1-[2-(trifluoromethyl)benzyl]-1H-indole Step 1

{[6-(3-Pentyl-1-[2-(trifluoromethyl)benzyl]-1H-indol-2-yl)-2-naphthyl]oxy}acetonitrile The title compound was prepared as a solid (0.147 g, 34%) from {[6-(3-pentyl-1H-indol-2-yl)-2-naphthyl]oxy}acetonitrile using 2-trifluoromethyl benzyl bromide and the procedure from step 4 of Example 2; $^1$H NMR (DMSO-d$_6$) δ 0.72 (t, J=7.8 Hz, 3H), 1.08–1.29 (m, 4H), 1.51–1.67 (m, 2H), 2.71 (t, J=8.6 Hz, 2H), 5.29 (s, 2H), 5.47 (s, 2H), 6.37 (d, J=8.6 Hz, 1H), 7.08–7.21 (m, 2H), 7.23–7.32 (m, 2H), 7.35–7.45 (m, 2H), 7.48 (t, J=7.8 Hz, 1H), 7.53 (d, J=1.7 Hz, 1H), 7.63–7.75 (m, 2H), 7.83–7.92 (m, 3H); mass spectrum [(+) ESI], m/z 527 (M+H)$^+$.

Step 2

3-Pentyl-2-[6-(1H-tetraazol-5-ylmethoxy)-2-naphthyl]-1-[2-(trifluoromethyl)benzyl]-1H-indole The title compound was prepared as a lt. brown/tan solid (0.097 g, 66%) from {[6-(3-pentyl-1-[2-(trifluoromethyl)benzyl]-1H-indol-2-yl)-2-naphthyl]oxy}acetonitrile using the procedure from step 5 of Example 2, mp>100° C. (decomp.); $^1$H NMR (DMSO-d$_6$) δ 0.73 (t, J=7.0 Hz, 3H), 1.11–1.27 (m, 4H), 1.53–1.63 (m, 2H), 2.70 (t, J=7.5 Hz, 2H), 5.46 (s, 2H), 5.60 (s, 2H), 6.36 (d, J=7.8 Hz, 1H), 7.09–7.17 (m, 2H), 7.24 (d, J=7.5 Hz, 1H), 7.28 (dd, J=2.4, 9.0 Hz, 1H), 7.34–7.40 (m, 2H), 7.46 (t, J=7.6 Hz, 1H), 7.52 (d, J=2.3 Hz, 1H), 7.64 (d, J=7.6 Hz, 1H), 7.67 (d, J=6.9 Hz, 1H), 7.79–7.85 (m, 3H), 16.15–17.50 (bs, 1H); IR (neat) 3040, 2950, 2930, 2860, 1630, 1605, 1570, 1480, 1460, 1445, 1390, 1340, 1310, 1255, 1230, 1205, 1165, 1120, 1060, 1035, 930, 900, 865, 805, 775, 745, 725, and 660 cm$^{-1}$; mass spectrum [(−) ESI], m/z 568(M−H)$^-$;

Anal. Calcd. for C$_{33}$H$_{30}$F$_3$N$_5$O·0.5H$_2$O: C, 68.50; H, 5.40; N, 12.10, Found: C, 68.63; H, 5.34; N, 11.87.

Example 8

2-[5-Bromo-6-(1H-tetraazol-5-ylmethoxy)-2-naphthyl]-3-pentyl-1-[2-(trifluoromethyl)benzyl]-1H-indole Step 1

{[6-(3-Pentyl-1-[2-(trifluoromethyl)benzyl]-1H-indol-2-yl)-1-bromo-2-naphthyl]oxy}acetonitrile The title compound was prepared as a solid (0.053 g, 14%) from {[1-bromo-6-(3-pentyl-1H-indol-2-yl)-2-naphthyl]oxy}acetonitrile using 2-trifluoromethyl benzyl bromide and the procedure from step 4 of Example 2; $^1$H NMR (DMSO-d$_6$) δ 0.72 (t, J=7.0 Hz, 3H), 1.11–1.22 (m, 4H), 1.54–1.62 (m, 2H), 2.71 (t, J=7.4 Hz, 2H), 5.42 (s, 2H), 5.48 (s, 2H), 6.34 (d, J=7.9 Hz, 1H), 7.11–7.20 (m, 2H), 7.28 (d, J=7.8 Hz, 1H), 7.37 (t, J=7.8 Hz, 1H), 7.45 (t, J=7.8 Hz, 1H), 7.57 (dd, J=1.7, 8.9 Hz, 1H), 7.63–7.68 (m, 2H), 7.69 (d, J=7.2 Hz, 1H), 7.95 (d, J=1.2 Hz, 1H), 8.03 (d, J=9.2 Hz, 1H), 8.12 (d, J=8.7 Hz, 1H).

Step 2

2-[5-Bromo-6-(1H-tetraazol-5-ylmethoxy)-2-naphthyl]-3-pentyl-1-[2-(trifluoromethyl)benzyl]-1H-indole The title compound was prepared as a yellow foam (0.013 g, 25%) from {[6-(3-pentyl-1-[2-(trifluoromethyl)benzyl]-1H-indol-2-yl)-1-bromo-2-naphthyl]oxy}-acetonitrile using the procedure from step 5 of Example 2, mp>85° C. (decomp.); $^1$H NMR (DMSO-d$_6$) δ 0.73 (t, J=6.9 Hz, 3H), 1.10–1.23 (m, 4H), 1.54–1.62 (m, 2H), 2.70 (t, J=7.33 Hz, 2H), 5.47 (s, 2H), 5.70 (s, 2H), 6.34 (d, J=7.8 Hz, 1H), 7.11–7.18 (m, 2H), 7.27 (d, J=7.6 Hz, 1H), 7.37 (t, J=7.5 Hz, 1H), 7.45 (t, J=7.6 Hz, 1H), 7.54 (dd, J=1.5, 8.7 Hz, 1H), 7.63 (d, J=7.6 Hz, 1H), 7.65–7.70 (m, 2H), 7.91 (d, J=1.4 Hz, 1H), 7.97 (d, J=9.0 Hz, 1H), 8.08 (d, J=8.7 Hz, 1H), 15.75–17.85 (bs, 1H); IR (neat) 3050, 2950, 2920, 2855, 1600, 1565, 1475, 1460, 1415, 1355, 1335, 1310, 1270, 1245, 1195, 1160, 1115, 1075, 1060, 1035, 970, 925, 895, 830, 795, 770, 740, and 650 cm$^{-1}$; mass spectrum [(+) ESI], m/z 648 (M+H)$^+$ and [(−) ESI], m/z 646 (M−H)$^-$;

Anal. Calcd. for C$_{33}$H$_{29}$BrF$_3$N$_5$O·3.3H$_2$O: C, 55.99; H, 5.07; N, 9.89, Found: C, 56.14; H, 4.36; N, 9.44.

Example 9

1-(4-tert-Butylbenzyl)-3-pentyl-2-[6-(1H-tetraazol-5-ylmethoxy)-2-naphthyl]-1H-indole Step 1

{[6-(1-[4-tert-Butylbenzyl]-3-pentyl-1H-indol-2-yl)-2-naphthyl]oxy}acetonitrile

The title compound was prepared as a solid (0.191 g, 46%) from {[6-(3-pentyl-1H-indol-2-yl)-2-naphthyl]oxy}acetonitrile using 4-tert-butylbenzyl bromide and the procedure from step 4 of Example 2; $^1$H NMR (DMSO-d$_6$) δ 0.73 (t, J=7.4 Hz, 3H), 1.08–1.27 (m, 4H), 1.17 (s, 9H), 1.48–1.65 (m, 2H), 2.69 (t, J=8.1 Hz, 2H), 5.29 (s, 2H), 5.52 (s, 2H), 6.78 (d, J=8.1 Hz, 2H), 7.05–7.14 (m, 2H), 7.18 (d, J=8.1 Hz, 2H), 7.32 (dd, J=1.4, 9.9 Hz, 1H), 7.38 (d, J=7.4, 1H), 7.53 (d, J=8.5 Hz, 1H), 7.58–7.67 (m, 2H), 7.90–8.00 (m, 3H); mass spectrum [(+) ESI], m/z 515 (M+H)$^+$, 537 (M+Na)$^+$ and [(−) ESI], m/z 513 (M−H)$^-$.

Step 2

1-(4-tert-Butylbenzyl)-3-pentyl-2-[6-(1H-tetraazol-5-ylmethoxy)-2-naphthyl]-1H-indole The title compound was prepared as a yellow foamy solid (0.144 g, 73%) from {[6-(1-[4-tert-butylbenzyl]-3-pentyl-1H-indol-2-yl)-2-naphthyl]oxy}acetonitrile using the procedure from step 5 of Example 2, mp>95° C. (decomp.); $^1$H NMR (DMSO-d$_6$) δ 0.73 (t, J=6.7 Hz, 3H), 1.12–1.20 (m, 4H), 1.16 (s, 9H), 1.52–1.58 (m, 2H), 2.67 (t, J=7.5 Hz, 2H), 5.26 (s, 2H), 5.60 (t, 2H), 6.76 (d, J=8.2 Hz, 2H), 7.05 (t, J=7.5 Hz, 1H), 7.10 (t, J=7.8 Hz, 1H), 7.17 (d, J=8.2 Hz, 2H), 7.30 (dd, J=2.3, 9.0 Hz, 1H), 7.35 (d, J=7.9 Hz, 1H), 7.47 (dd, J=1.2, 8.6 Hz, 1H), 7.56 (d, J=2.3 Hz, 1H), 7.59 (d, J=7.8 Hz, 1H), 7.87–7.92 (m, 3H), 14.75–17.75 (bs, 1H); IR (neat) 3060, 2950, 2925, 2850, 1630, 1605, 1565, 1515, 1500, 1480, 1465, 1445, 1410, 1395, 1365, 1345, 1305, 1270, 1235, 1200, 1170, 1130, 1105, 1030, 1010, 965, 930, 900, 855, 810, 740, and 670 cm$^{-1}$; mass spectrum [(−) ESI], m/z 556 (M−H)$^-$;

Anal. Calcd. for $C_{36}H_{39}N_5O \cdot 0.75H_2O$: C, 75.69; H, 7.15; N, 12.26, Found: C, 75.84; H, 6.92; N, 12.30.

Example 10

2-[5-Bromo-6-(1H-tetraazol-5-ylmethoxy)-2-naphthyl]-1-(4-tert-butylbenzyl)-3-pentyl-1H-indole Step 1
{[6-(1-[-4-tert-Butylbenzyl]-3-pentyl-1H-indol-2-yl)-1-bromo-2-naphthyl]oxy}acetonitrile The title compound was prepared as a solid (0.070 g, 19%) from {[1-bromo-6-(3-pentyl-1H-indol-2-yl)-2-naphthyl]oxy}acetonitrile using 4-tert-butylbenzyl bromide and the procedure from step 4 of Example 2; $^1$H NMR (DMSO-$d_6$) δ 0.73 (t, J=7.3 Hz, 3H), 1.06–1.30 (m, 4H), 1.15 (s, 9H), 1.48–1.63 (m, 2H), 2.69 (t, J=8.4 Hz, 1H), 5.31 (s, 2H), 5.47 (s, 2H), 6.74 (d, J=8.4 Hz, 2H), 7.05–7.17 (m, 3H), 7.17 (d, J=8.4 Hz, 2H), 7.42 (d, J=8.7 Hz, 1H), 7.66 (d, J=8.0 Hz, 1H), 7.70 (d, J=9.1 Hz, 2H), 8.05 (s, 1H), 8.13 (d, J=8.0 Hz, 1H), 8.23 (d, J=8.0 Hz, 1H); mass spectrum [(+) ESI], m/z 593/595 (M+H)$^+$.

Step 2
2-[5-Bromo-6-(1H-tetraazol-5-ylmethoxy)-2-naphthyl]-1-(4-tert-butylbenzyl)-3-pentyl-1H-indole The title compound was prepared as a yellow foam (0.042 g, 56%) from {[6-(1-[-4-tert-butylbenzyl]-3-pentyl-1H-indol-2-yl)-1-bromo-2-naphthyl]oxy}acetonitrile using the procedure from step 5 of Example 2, mp>90° C. (decomp.); $^1$H NMR (DMSO-$d_6$) δ 0.72 (t, J=7.0 Hz, 3H), 1.11–1.18 (m, 4H), 1.15 (s, 9H), 1.52–1.58 (m, 2H), 2.68 (t, J=7.3 Hz, 2H), 5.28 (s, 2H), 5.72 (s, 2H), 6.74 (d, J=8.2 Hz, 2H), 7.06 (t, J=7.2 Hz, 1H), 7.11 (t, J=7.6 Hz, 1H), 7.17 (d, J=8.2 Hz, 2H), 7.38 (d, J=8.1 Hz, 1H), 7.61 (d, J=7.6 Hz, 1H), 7.65 (dd, J=1.7, 8.9 Hz 1H), 7.71 (d, J=9.2 Hz, 1H), 7.98 (d, J=1.4 Hz, 1H), 8.04 (d, J=9.2 Hz, 1H), 8.17 (d, J=8.7 Hz, 1H), 14.85–17.55 (bs, 1H); IR (neat) 3130, 3055, 2960, 2925, 2855, 2620, 1600, 1565, 1515, 1480, 1465, 1445, 1410, 1395, 1365, 1330, 1305, 1270, 1245, 1195, 1145, 1105, 1050, 1015, 975, 920, 895, 825, 800, 760, 740, 700, and 665 cm$^{-1}$; mass spectrum [(−) ESI], m/z 634/636 (M−H)$^-$;

Anal. Calcd. for $C_{36}H38BrN_5O \cdot 1.25H_2O$: C, 65.60; H, 6.19; N, 10.62, Found: C, 65.49; H, 5.92; N, 10.29.

Example 11

{[1-Bromo-6-(1-methyl-3-pentyl-1H-indol-2-yl)-2-naphthyl]oxy}acetic acid

Step 1
{[1-Bromo-6-(3-pentyl-1H-indol-2-yl)-2-naphthyl]oxy}acetic acid methyl ester The title compound was prepared as a solid (0.410 g, 58%) from 2-(5-bromo-6-hydroxy-2-naphthyl)-3-pentyl-1H-indole using methyl bromoacetate and the procedure from step 3 of Example 2; $^1$H NMR (DMSO-$d_6$) δ 0.82 (t, J=7.0 Hz, 3H), 1.27–1.39 (m, 4H), 1.64–1.74 (m, 2H), 2.93 (t, J=7.3 Hz, 2H), 3.73 (s, 3H), 5.12 (s, 2H), 7.02 (t, J=7.5 Hz, 1H), 7.12 (t, J=7.0 Hz, 1H), 7.38 (d, J=8.0 Hz, 1H), 7.48 (d, J=9.2 Hz, 1H), 7.57 (d, J=7.9 Hz, 1H), 7.93 (d, J=7.9 Hz, 1H), 8.03 (d, J=9.0 Hz, 1H), 8.14 (d, J=1.6 Hz, 1H), 8.22 (d, J=8.9 Hz, 1H), 11.26 (s, 1H); mass spectrum [(+) ESI], m/z 480/482 (M+H)$^+$ and [(−) ESI], m/z 478/480 (M−H)$^-$.

Step 2
{[1-Bromo-6-(1-methyl-3-pentyl-1H-indol-2-yl)-2-naphthyl]oxy}acetic acid

To a stirred solution of {[1-bromo-6-(3-pentyl-1H-indol-2-yl)-2-naphthyl]oxy}acetic acid methyl ester (0.410 g, 0.853 mmol) in THF (20 mL) at 0° C. was added KOt-Bu (0.105 g, 0.938 mmol) followed by MeI (0.064 mL, 1.02 mmol). The reaction was warmed to rt and let stir for 1 h. It appeared by TLC and MS that all the starting material was gone; however, two polar acids (one N—Me and one N—H) had been generated due to hydrolysis in these basic conditions. After concentration, the residue was taken up in DMF (20 mL). Added NaH (0.075 g, 60% by wt., 1.88 mmol) followed by excess MeI to convert all intermediate to one acid (N—Me). After 1 h, the reaction mixture was concentrated and then diluted with EtOAc (200 mL) and 1 N HCl (20 mL). The organic layer was washed with $H_2O$ (20 mL) and brine (20 mL) and then dried ($Na_2SO_4$). After concentration, the residue was purified by preparatory plate chromatography (10% MeOH:CHCl$_3$) to afford the product (0.232 g, 57%) as a yellowish-orange foamy solid, mp>73° C. (decomp.); $^1$H NMR (DMSO-$d_6$) δ 0.73 (t, J=7.0 Hz, 3H), 1.11–1.20 (m, 4H), 1.50–1.58 (m, 2H), 2.66 (t, J=7.3 Hz, 2H), 3.58 (s, 3H), 4.93 (s, 2H), 7.07 (t, J=7.6 Hz, 1H), 7.19 (t, J=7.1 Hz, 1H), 7.42–7.48 (m, 2H), 7.58 (d, J=7.9 Hz, 1H), 7.68 (dd, J=1.7, 8.7 Hz, 1H), 7.99 (s, 1H), 8.04 (d, J=9.0 Hz, 1H), 8.21 (d, J=8.7 Hz, 1H), 11.95–14.75 (bs, 1H); IR (neat) 3050, 2955, 2925, 2850, 1725, 1670, 1600, 1480, 1470, 1430, 1370, 1325, 1275, 1220, 1190, 1145, 1095, 1015, 980, 925, 895, 830, 800, 765, 735, 700, and 665 cm$^{-1}$; mass spectrum [(+) ESI], m/z 480/482 (M+H)$^+$;

Anal. Calcd. for $C_{26}H_{26}BrNO_3 \cdot 0.5H_2O$: C, 63.81; H, 5.56; N, 2.86, Found: C, 63.67; H, 5.30; N, 2.77.

What is claimed is:
1. A method for treatment of thrombosis or fibrinolytic impairment in a mammal, the method comprising administering to a mammal in need thereof a pharmaceutically effective amount of a compound of Formula I:

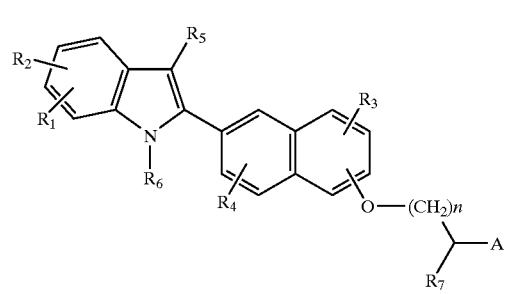

wherein:
$R_1$, $R_2$, and $R_3$, are each, independently, hydrogen, alkyl of 1–3 carbons, cycloalkyl of 3–5 carbon atoms, —CH$_2$-cycloalkyl of 3–5 carbon atoms, alkanoyl of 1–3 carbons, halogen, hydroxy, aryl optionally substituted with from 1 to 3 groups selected from $R_8$, perfluoroalkyl of 1–3 carbons, alkoxy of 1–3 carbons, amino, alkylamino of 1–3 carbons, dialkylamino of 1–3 carbons, or perfluoroalkoxy of 1–3 carbons;

$R_5$ is hydrogen, alkyl of 1–6 carbons, perfluoroalkyl of 1–6 carbons, aryl substituted with $R_8$, alkanoyl of 1–6 carbons, or aroyl optionally substituted with from 1 to 3 groups selected from $R_8$;

$R_6$ is hydrogen, alkyl of 1–6 carbons, alkylaryl, benzyl substituted with $R_8$, alkanoyl of 1–6 carbons, or aroyl optionally substituted with from 1 to 3 groups selected from $R_8$;

$R_7$ is hydrogen, alkyl of 1–6 carbons, alkylaryl, or aryl optionally substituted with from 1 to 3 groups selected from $R_8$;

n is an integer of 0–6;

A is COOH, or an acid mimic;

$R_8$ is hydrogen, alkyl of 1–3 carbons, cycloalkyl of 3–5 carbons, —CH$_2$-cycloalkyl of 3–5 carbon atoms, alkanoyl of 1–3 carbons, halogen, hydroxy, perfluoroalkyl of 1–3 carbons, alkoxy of 1–3 carbons, amino, alkylamino of 1–3 carbons, dialkylamino of 1–3 carbons, or perfluoroalkoxy of 1–3 carbons;

or a pharmaceutically acceptable salt or ester form thereof.

2. A method of claim 1 wherein the thrombosis or fibrinolytic impairment is associated with formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery or peripheral arterial occlusion.

3. A method for the treatment of deep vein thrombosis in a mammal, comprising administering to a mammal in need thereof a pharmaceutically effective amount of a compound of Formula I:

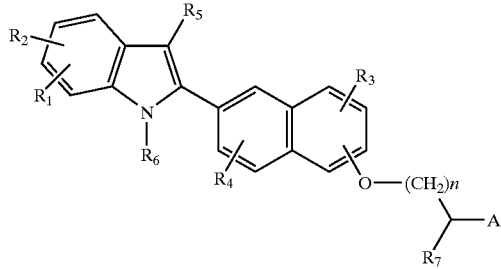

wherein:

$R_1$, $R_2$, and $R_3$, are each, independently, hydrogen, alkyl of 1–3 carbons, cycloalkyl of 3–5 carbon atoms, —CH$_2$-cycloalkyl of 3–5 carbon atoms, alkanoyl of 1–3 carbons, halogen, hydroxy, aryl optionally substituted with from 1 to 3 groups selected from $R_8$, perfluoroalkyl of 1–3 carbons, alkoxy of 1–3 carbons, amino, alkylamino of 1–3 carbons, dialkylamino of 1–3 carbons, or perfluoroalkoxy of 1–3 carbons;

$R_5$ is hydrogen, alkyl of 1–6 carbons, perfluoroalkyl of 1–6 carbons, aryl substituted with $R_8$, alkanoyl of 1–6 carbons, or aroyl optionally substituted with from 1 to 3 groups selected from $R_8$;

$R_6$ is hydrogen, alkyl of 1–6 carbons, alkylaryl, benzyl substituted with $R_8$, alkanoyl of 1–6 carbons, or aroyl optionally substituted with from 1 to 3 groups selected from $R_8$;

$R_7$ is hydrogen, alkyl of 1–6 carbons, alkylaryl, or aryl optionally substituted with from 1 to 3 groups selected from $R_8$;

n is an integer of 0–6;

A is COOH, or an acid mimic;

$R_8$ is hydrogen, alkyl of 1–3 carbons, cycloalkyl of 3–5 carbons, —CH$_2$-cycloalkyl of 3–5 carbon atoms, alkanoyl of 1–3 carbons, halogen, hydroxy, perfluoroalkyl of 1–3 carbons, alkoxy of 1–3 carbons, amino, alkylamino of 1–3 carbons, dialkylamino of 1–3 carbons, or perfluoroalkoxy of 1–3 carbons;

or a pharmaceutically acceptable salt or ester form thereof.

4. A method for the treatment of renal fibrosis in a mammal, comprising administering to a mammal in need thereof a pharmaceutically effective amount of a compound of Formula I:

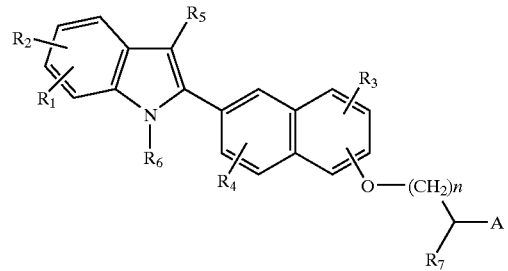

wherein:

$R_1$, $R_2$, and $R_3$, are each, independently, hydrogen, alkyl of 1–3 carbons, cycloalkyl of 3–5 carbon atoms, —CH$_2$-cycloalkyl of 3–5 carbon atoms, alkanoyl of 1–3 carbons, halogen, hydroxy, aryl optionally substituted with from 1 to 3 groups selected from $R_8$, perfluoroalkyl of 1–3 carbons, alkoxy of 1–3 carbons, amino, alkylamino of 1–3 carbons, dialkylamino of 1–3 carbons, or perfluoroalkoxy of 1–3 carbons;

$R_5$ is hydrogen, alkyl of 1–6 carbons, perfluoroalkyl of 1–6 carbons, aryl substituted with $R_8$, alkanoyl of 1–6 carbons, or aroyl optionally substituted with from 1 to 3 groups selected from $R_8$;

$R_6$ is hydrogen, alkyl of 1–6 carbons, alkylaryl, benzyl substituted with $R_8$, alkanoyl of 1–6 carbons, or aroyl optionally substituted with from 1 to 3 groups selected from $R_8$;

$R_7$ is hydrogen, alkyl of 1–6 carbons, alkylaryl, or aryl optionally substituted with from 1 to 3 groups selected from $R_8$;

n is an integer of 0–6;

A is COOH, or an acid mimic;

$R_8$ is hydrogen, alkyl of 1–3 carbons, cycloalkyl of 3–5 carbons, —CH$_2$-cycloalkyl of 3–5 carbon atoms, alkanoyl of 1–3 carbons, halogen, hydroxy, perfluoroalkyl of 1–3 carbons, alkoxy of 1–3 carbons, amino, alkylamino of 1–3 carbons, dialkylamino of 1–3 carbons, or perfluoroalkoxy of 1–3 carbons;

or a pharmaceutically acceptable salt or ester form thereof.

5. The method of claim 1 wherein A is COOH, tetrazole, SO$_3$H, PO$_3$H$_2$, tetronic acid, or groups having the formula:

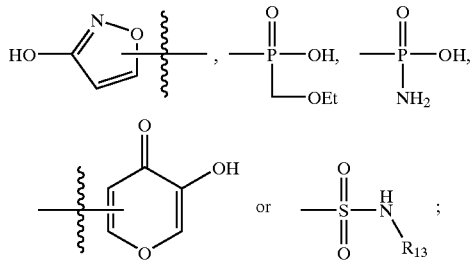

wherein $R_{13}$ is $C_1$–$C_6$ alkyl, $C_2$–$C_6$ alkenyl, $C_3$–$C_6$ cycloalkyl, —CH$_2$—($C_3$–$C_6$ cycloalkyl), $C_3$–$C_6$ cycloalkenyl, —CH$_2$—($C_3$–$C_6$ cycloalkenyl), aryl, heteroaryl, —$C_1$–$C_6$ alkyl-aryl or —$C_1$–$C_6$ alkyl-heteroaryl.

6. The method of claim 1 wherein the compound of Formula I is
- 1-Benzyl-3-pentyl-2-[6-(1H-tetraazol-5-ylmethoxy)-2-naphthyl]-1H-indole;
- 6-(1-Benzyl-3-pentyl-1H-indol-2-yl)-1-bromo-2-naphthyl 1H-tetraazol-5-ylmethyl ether;
- 1-Benzyl-2-[5-bromo-6-(1H-tetraazol-5-ylmethoxy)-2-naphthyl]-3-pentyl-1H-indole;
- 1-Methyl-3-pentyl-2-[6-(1H-tetraazol-5-ylmethoxy)-2-naphthyl]-1H-indole;
- 2-[5-Bromo-6-(1H-tetraazol-5-ylmethoxy)-2-naphthyl]-1-methyl-3-pentyl-1H-indole;
- 1-Bromo-6-(1-methyl-3-pentyl-1H-indol-2-yl)-2-naphthyl 1H-tetraazol-5-ylmethyl ether;
- 1-Acetyl-3-pentyl-2-[6-(1H-tetraazol-5-ylmethoxy)-2-naphthyl]-1H-indole;
- 1-Acetyl-2-[5-bromo-6-(1H-tetraazol-5-ylmethoxy)-2-naphthyl]-3-pentyl-1H-indole;
- 3-Pentyl-2-[6-(1H-tetraazol-5-ylmethoxy)-2-naphthyl]-1-[2-(trifluoromethyl)benzyl]-1H-indole;
- 2-[5-Bromo-6-(1H-tetraazol-5-ylmethoxy)-2-naphthyl]-3-pentyl-1-[2-(trifluoromethyl)benzyl]-1H-indole;
- 1-(4-tert-Butylbenzyl)-3-pentyl-2-[6-(1H-tetraazol-5-ylmethoxy)-2-naphthyl]-1H-indole;
- 2-[5-Bromo-6-(1H-tetraazol-5-ylmethoxy)-2-naphthyl]-1-(4-tert-butylbenzyl)-3-pentyl-1H-indole;
- {[1-Bromo-6-(1-methyl-3-pentyl-1H-indol-2-yl)-2-naphthyl]oxy}acetic acid;

or pharmaceutically acceptable salt thereof.

7. The method of claim 3 wherein A is COOH, tetrazole, SO$_3$H, PO$_3$H$_2$, tetronic acid, or groups having the formula:

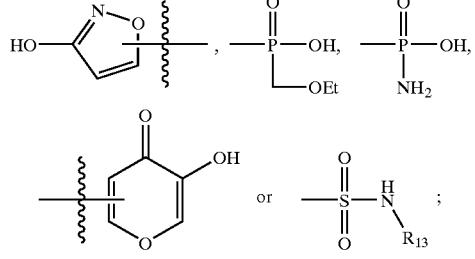

wherein R$_{13}$ is C$_1$–C$_6$ alkyl, C$_2$–C$_6$ alkenyl, C$_3$–C$_6$ cycloalkyl, —CH$_2$—(C$_3$–C$_6$ cycloalkyl), C$_3$–C$_6$ cycloalkenyl, —CH$_2$—(C$_3$–C$_6$ cycloalkenyl), aryl, heteroaryl, —C$_1$–C$_6$ alkyl-aryl or —C$_1$–C$_6$ alkyl-heteroaryl.

8. The method of claim 3 wherein the compound of Formula I is
- 1-Benzyl-3-pentyl-2-[6-(1H-tetraazol-5-ylmethoxy)-2-naphthyl]-1H-indole;
- 6-(1-Benzyl-3-pentyl-1H-indol-2-yl)-1-bromo-2-naphthyl 1H-tetraazol-5-ylmethyl ether;
- 1-Benzyl-2-[5-bromo-6-(1H-tetraazol-5-ylmethoxy)-2-naphthyl]-3-pentyl-1H-indole;
- 1-Methyl-3-pentyl-2-[6-(1H-tetraazol-5-ylmethoxy)-2-naphthyl]-1H-indole;
- 2-[5-Bromo-6-(1H-tetraazol-5-ylmethoxy)-2-naphthyl]-1-methyl-3-pentyl-1H-indole;
- 1-Bromo-6-(1-methyl-3-pentyl-1H-indol-2-yl)-2-naphthyl 1H-tetraazol-5-ylmethyl ether;
- 1-Acetyl-3-pentyl-2-[6-(1H-tetraazol-5-ylmethoxy)-2-naphthyl]-1H-indole;
- 1-Acetyl-2-[5-bromo-6-(1H-tetraazol-5-ylmethoxy)-2-naphthyl]-3-pentyl-1H-indole;
- 3-Pentyl-2-[6-(1H-tetraazol-5-ylmethoxy)-2-naphthyl]-1-[2-(trifluoromethyl)benzyl]-1H-indole;
- 2-[5-Bromo-6-(1H-tetraazol-5-ylmethoxy)-2-naphthyl]-3-pentyl-1-[2-(trifluoromethyl)benzyl]-1H-indole;
- 1-(4-tert-Butylbenzyl)-3-pentyl-2-[6-(1H-tetraazol-5-ylmethoxy)-2-naphthyl]-1H-indole;
- 2-[5-Bromo-6-(1H-tetraazol-5-ylmethoxy)-2-naphthyl]-1-(4-tert-butylbenzyl)-3-pentyl-1H-indole;
- {[1-Bromo-6-(1-methyl-3-pentyl-1H-indol-2-yl)-2-naphthyl]oxy}acetic acid;

or pharmaceutically acceptable salt thereof.

9. The method of claim 4 wherein A is COOH, tetrazole, SO$_3$H, PO$_3$H$_2$, tetronic acid, or groups having the formula:

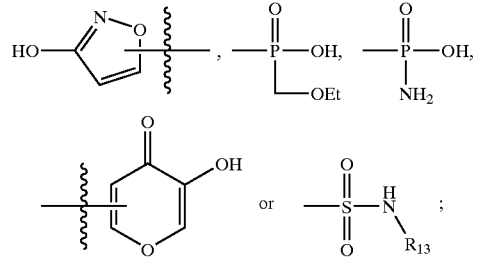

wherein R$_{13}$ is C$_1$–C$_6$ alkyl, C$_2$–C$_6$ alkenyl, C$_3$–C$_6$ cycloalkyl, —CH$_2$—(C$_3$–C$_6$ cycloalkyl), C$_3$–C$_6$ cycloalkenyl, —CH$_2$—(C$_3$–C$_6$ cycloalkenyl), aryl, heteroaryl, —C$_1$–C$_6$ alkyl-aryl or —C$_1$–C$_6$ alkyl-heteroaryl.

10. The method of claim 4 wherein the compound of Formula I is
- 1-Benzyl-3-pentyl-2-[6-(1H-tetraazol-5-ylmethoxy)-2-naphthyl]-1H-indole;
- 6-(1-Benzyl-3-pentyl-1H-indol-2-yl)-1-bromo-2-naphthyl 1H-tetraazol-5-ylmethyl ether;
- 1-Benzyl-2-[5-bromo-6-(1H-tetraazol-5-ylmethoxy)-2-naphthyl]-3-pentyl-1H-indole;
- 1-Methyl-3-pentyl-2-[6-(1H-tetraazol-5-ylmethoxy)-2-naphthyl]-1H-indole;
- 2-[5-Bromo-6-(1H-tetraazol-5-ylmethoxy)-2-naphthyl]-1-methyl-3-pentyl-1H-indole;
- 1-Bromo-6-(1-methyl-3-pentyl-1H-indol-2-yl)-2-naphthyl 1H-tetraazol-5-ylmethyl ether;
- 1-Acetyl-3-pentyl-2-[6-(1H-tetraazol-5-ylmethoxy)-2-naphthyl]-1H-indole;
- 1-Acetyl-2-[5-bromo-6-(1H-tetraazol-5-ylmethoxy)-2-naphthyl]-3-pentyl-1H-indole;
- 3-Pentyl-2-[6-(1H-tetraazol-5-ylmethoxy)-2-naphthyl]-1-[2-(trifluoromethyl)benzyl]-1H-indole;
- 2-[5-Bromo-6-(1H-tetraazol-5-ylmethoxy)-2-naphthyl]-3-pentyl-1-[2-(trifluoromethyl)benzyl]-1H-indole;
- 1-(4-tert-Butylbenzyl)-3-pentyl-2-[6-(1H-tetraazol-5-ylmethoxy)-2-naphthyl]-1H-indole;
- 2-[5-Bromo-6-(1H-tetraazol-5-ylmethoxy)-2-naphthyl]-1-(4-tert-butylbenzyl)-3-pentyl-1H-indole;
- {[1-Bromo-6-(1-methyl-3-pentyl-1H-indol-2-yl)-2-naphthyl]oxy}acetic acid;

or pharmaceutically acceptable salt thereof.

* * * * *

UNITED STATES PATENT AND TRADEMARK OFFICE
CERTIFICATE OF CORRECTION

PATENT NO. : 6,939,886 B2
APPLICATION NO. : 10/894618
DATED : September 6, 2005
INVENTOR(S) : Scott Christian Mayer et al.

It is certified that error appears in the above-identified patent and that said Letters Patent is hereby corrected as shown below:

Column 29, lines 24-27; column 30, lines 7-11 and column 30, lines 58-62: please delete the following text from each of claims 6, 8 and 10:

"1-(4-tert-Butylbenzyl)-3-pentyl-2-[6-(1H-tetraazol-5-ylmethoxy)-2-naphthyl]-1H-indole; 2-[5-Bromo-6-(1H-tetraazol-5-ylmethoxy)-2-naphthyl]-1-(4-tert-butylbenzyl)-3-pentyl-1H-indole;".

Signed and Sealed this

Twenty-fourth Day of March, 2009

JOHN DOLL
*Acting Director of the United States Patent and Trademark Office*